US009206439B2

(12) United States Patent
Lindner et al.

(10) Patent No.: US 9,206,439 B2
(45) Date of Patent: Dec. 8, 2015

(54) EFFICIENT *ORIP*/EBNA-1 PLASMID VECTOR

(75) Inventors: Scott Eugene Lindner, Fitchburg, WI (US); William M. Sugden, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1429 days.

(21) Appl. No.: 12/353,835

(22) Filed: Jan. 14, 2009

(65) Prior Publication Data
US 2009/0203545 A1 Aug. 13, 2009

Related U.S. Application Data

(60) Provisional application No. 61/020,918, filed on Jan. 14, 2008.

(51) Int. Cl.
| | |
|---|---|
| *C12N 15/00* | (2006.01) |
| *C07H 21/02* | (2006.01) |
| *G01N 33/00* | (2006.01) |
| *C40B 40/00* | (2006.01) |
| *C12N 5/07* | (2010.01) |
| *A01N 63/00* | (2006.01) |
| *C12N 15/85* | (2006.01) |

(52) U.S. Cl.
CPC ...... *C12N 15/85* (2013.01); *C12N 2710/16222* (2013.01); *C12N 2820/60* (2013.01)

(58) Field of Classification Search
CPC ................... C12N 15/85; C12N 2710/16222; C12N 2820/60
See application file for complete search history.

(56) References Cited

U.S. PATENT DOCUMENTS

2005/0260564 A1 11/2005 Sugden

OTHER PUBLICATIONS

Almqvist et al. (Functional interaction of Oct transcription factors with the family of repeats in Epstein-Barr virus oriP, 2005, Journal of General Virology, vol. 86, pp. 1261-1267).*
"International Application Serial No. PCT/US2009/000220, International Search Report mailed May 4, 2009", 5 pgs.
"International Application Serial No. PCT/US2009/000220, International Written Opinion mailed May 4, 2009", 9 pgs.
Atanasiu, C., et al., "ORC binding to TRF2 stimulates OriP replication", *EMBO Reports*, 7(7), (Jul. 2006), 716-721
Deng, Z., et al., "Telomere Repeat Binding Factors TRFI, TRF2, and hRAP I Modulate Replication of Epstein-Barr Virus OriP", *Journal of Virology*, 77(22), (Nov. 2003), 11992-12001.
Lindner, S., et al., "The Affinity of EBNA1 for its Origin of DNA Synthesis Is a Determinant of the Origin's Replicative Efficiency", *Journal of Virology*, 82(17), (Mar. 24, 2008), 5693-5702.
Lindner, S. E., et al., "The plasmid replicon of Epstein-Barr virus: Mechanistic insights", *Plasmid*, 58(1), (2007), 1-12.

* cited by examiner

*Primary Examiner* — Reza Ghafoorian
(74) *Attorney, Agent, or Firm* — Schwegman Lundberg & Woessner, P.A.

(57) ABSTRACT

The invention provides a recombinant vector comprising a DNA segment having a synthetic origin of DNA synthesis that binds EBNA-1 and is capable of initiating DNA synthesis of sequences linked to the synthetic origin of DNA synthesis and maintaining the linked sequences when in the presence of EBNA-1. The synthetic origin of DNA synthesis comprises at least two binding sites for EBNA-1, wherein the two EBNA-1 binding sites are flanked by at least two half-binding sites for TRF2 or at least two binding sites for a protein that enhances the affinity of EBNA-1 for the synthetic origin of DNA synthesis. Further provided are host cells with the vector and methods of using the vector, for instance, ex vivo or in vivo.

43 Claims, 6 Drawing Sheets

MAPPGMRLRS GRSTGAPLTR GSCRKRNRSP ERCDLGDDLH LQPRRKHVAD
SVDGRECGPHTLPIPGSPTV FTSGLPAFVS SPTLPVAPIP SPAPATPLPP
PALLPPVTTS SSPIPPSHPVSPGTTDTHSP SPALPPTQSP ESSQRPPLSS
PTGRPDSSTP MRPPPSQQTT PPHSPTTPPPEPPSKSSPDS LAPSTLRSLR
KRRLSSPQGP STLNPICQSP PVSPPRCDFA NRSVYPPWATESPIYVGSSS
DGDTPPRQPP TSPISIGSSS PSEGSWGDDT AMLVLLAEIA EEASKNEKEC
SENNQAGEDN GDNEISKESQ VDKDDNDNKD DEEEQETDEE DEEDDEEDDE
EDDEEDDEEDDEEDDEEDDE EEDEEEDEEE DEEEDEEEEE DEEDDDDEDN
EDEEDDEEED KKEDEEDGGDGNKTLSIQSS QQQQEPQQQE PQQQEPQQQE
PQQQEPQQQE PQQQEPQQQE PQQREPQQREPQQREPQQRE PQQREPQQRE
PQQREPQQRE PQQREPQQRE PQQREPQQRE PQQQEPQQQEPQQQEPQQQE
PQQQEPQQQE PQQQEPQQQE PQQQEPQQQE PQQQEPQQQE PQQQDEQQQD
EQQQDEQQQD EQQQDEQQQD EQQQDEQQQD EQEQQDEQQQ DEQQQQDEQE
QQEEQEQQEEQQQDEQQQDE QQQDEQQQDE QEQQDEQQQD EQQQQDEQEQ
QEEQEQQEEQ EQQEEQEQQEEQEQELEEQE QELEEQEQEL EEQEQELEEQ
EQELEEQEQE LEEQEQELEE QEQELEEQEQELEEQEQELE EQEQELEEQE
QELEEQEQEL EEQEQELEEQ EQEQELEEVE EQEQEQEEQE
LEEVEEQEQE QEEQEEQELE EVEEQEEQEL EEVEEQEEQE LEEVEEQEQQ
GVEQQEQETVEEPIILHGSS SEDEMEVDYP VVSTHEQIAS SPPGDNTPDD
DPQPGPSREY RYVLRTSPPHRPGVRMRRVP VTHPKKPHPR YQQPPVPYRQ
IDDCPAKARP QHIFYRRFLG KDGRRDPKCQWKFAVIFWGN DPYGLKKLSQ
AFQFGGVKAG PVSCLPHPGP DQSPITYCVY VYCQNKDTSK
KVQMARLAWE ASHPLAGNLQ SSIVKFKKPL PLTQPGENQG PGDSPQEMT (SEQ ID NO:35)

*Fig. 6*

SEQUENCE LISTING

```
<160> NUMBER OF SEQ ID NOS: 46

<210> SEQ ID NO 1
<211> LENGTH: 641
<212> TYPE: PRT
<213> ORGANISM: Artificial Sequence
<220> FEATURE:
<223> OTHER INFORMATION: A synthetic oligopeptide

<400> SEQUENCE: 1

Met Ser Asp Glu Gly Pro Gly Thr Gly Pro Gly Asn Gly Leu Gly Glu
1               5                   10                  15

Lys Gly Asp Thr Ser Gly Pro Glu Gly Ser Gly Gly Ser Gly Pro Gln
            20                  25                  30

Arg Arg Gly Gly Asp Asn His Gly Arg Gly Arg Gly Arg Gly Arg Gly
        35                  40                  45

Arg Gly Gly Gly Arg Pro Gly Ala Pro Gly Gly Ser Gly Ser Gly Pro
    50                  55                  60
```

```
Arg His Arg Asp Gly Val Arg Pro Gln Lys Arg Pro Ser Cys Ile
 65                  70                  75                  80

Gly Cys Lys Gly Thr His Gly Thr Gly Ala Gly Ala Gly Ala Gly
                 85                  90                  95

Gly Ala Gly Ala Gly Gly Ala Gly Ala Gly Gly Ala Gly Ala Gly
                100                 105                 110

Gly Gly Ala Gly Gly Ala Gly Ala Gly Gly Ala Gly Ala Gly Gly
                115                 120                 125

Gly Ala Gly Ala Gly Gly Gly Ala Gly Gly Ala Gly Ala Gly Ala
                130                 135                 140

Gly Gly Gly Ala Gly Ala Gly Gly Ala Gly Gly Ala Gly Ala Gly
145                 150                 155                 160

Gly Gly Ala Gly Gly Ala Gly Gly Ala Gly Ala Gly Gly Ala Gly
                165                 170                 175

Ala Gly Gly Ala Gly Gly Ala Gly Ala Gly Gly Ala Gly Ala Gly
                180                 185                 190

Ala Gly Gly Ala Gly Ala Gly Gly Gly Ala Gly Ala Gly Ala Gly
                195                 200                 205

Gly Ala Gly Gly Ala Gly Ala Gly Gly Ala Gly Ala Gly Gly Ala
                210                 215                 220

Gly Gly Ala Gly Gly Ala Gly Ala Gly Gly Ala Gly Ala Gly Ala
225                 230                 235                 240

Gly Ala Gly Gly Ala Gly Ala Gly Gly Ala Gly Gly Ala Gly Ala
                245                 250                 255

Gly Ala Gly Gly Ala Gly Ala Gly Gly Ala Gly Ala Gly Ala Gly
                260                 265                 270

Gly Gly Ala Gly Gly Ala Gly Ala Gly Gly Gly Ala Gly Ala Gly
                275                 280                 285

Ala Gly Gly Ala Gly Gly Ala Gly Ala Gly Gly Ala Gly Ala Gly
                290                 295                 300

Ala Gly Gly Ala Gly Gly Ala Gly Ala Gly Gly Ala Gly Ala Gly
305                 310                 315                 320

Gly Ala Gly Ala Gly Gly Gly Arg Gly Arg Gly Gly Ser Gly Gly
                325                 330                 335

Arg Gly Arg Gly Gly Ser Gly Gly Arg Gly Arg Gly Ser Gly Gly
                340                 345                 350

Arg Arg Gly Arg Gly Arg Glu Arg Ala Arg Gly Gly Ser Arg Glu Arg
                355                 360                 365

Ala Arg Gly Arg Gly Arg Gly Arg Gly Glu Lys Arg Pro Arg Ser Pro
                370                 375                 380

Ser Ser Gln Ser Ser Ser Ser Gly Ser Pro Pro Arg Pro Pro Pro
385                 390                 395                 400

Gly Arg Arg Pro Phe Phe His Pro Val Gly Glu Ala Asp Tyr Phe Glu
                405                 410                 415

Tyr His Gln Glu Gly Gly Pro Asp Gly Glu Pro Asp Val Pro Pro Gly
                420                 425                 430

Ala Ile Glu Gln Gly Pro Ala Asp Asp Pro Gly Glu Gly Pro Ser Thr
                435                 440                 445

Gly Pro Arg Gly Gln Gly Asp Gly Gly Arg Arg Lys Lys Gly Gly Trp
                450                 455                 460

Phe Gly Lys His Arg Gly Gln Gly Gly Ser Asn Pro Lys Phe Glu Asn
465                 470                 475                 480
```

-continued

```
Ile Ala Glu Gly Leu Arg Ala Leu Leu Ala Arg Ser His Val Glu Arg
                485                 490                 495
Thr Thr Asp Glu Gly Thr Trp Val Ala Gly Val Phe Val Tyr Gly Gly
            500                 505                 510
Ser Lys Thr Ser Leu Tyr Asn Leu Arg Arg Gly Thr Ala Leu Ala Ile
        515                 520                 525
Pro Gln Cys Arg Leu Thr Pro Leu Ser Arg Leu Pro Phe Gly Met Ala
    530                 535                 540
Pro Gly Pro Gly Pro Gln Pro Gly Pro Leu Arg Glu Ser Ile Val Cys
545                 550                 555                 560
Tyr Phe Met Val Phe Leu Gln Thr His Ile Phe Ala Glu Val Leu Lys
                565                 570                 575
Asp Ala Ile Lys Asp Leu Val Met Thr Lys Pro Ala Pro Thr Cys Asn
            580                 585                 590
Ile Arg Val Thr Val Cys Ser Phe Asp Asp Gly Val Asp Leu Pro Pro
        595                 600                 605
Trp Phe Pro Pro Met Val Glu Gly Ala Ala Ala Glu Gly Asp Asp Gly
    610                 615                 620
Asp Asp Gly Asp Glu Gly Gly Asp Gly Asp Glu Gly Glu Glu Gly Gln
625                 630                 635                 640
Glu

<210> SEQ ID NO 2
<211> LENGTH: 23
<212> TYPE: DNA
<213> ORGANISM: Artificial Sequence
<220> FEATURE:
<223> OTHER INFORMATION: A synthetic primer

<400> SEQUENCE: 2
cagatatcaa gcttgttaac cct                                          23

<210> SEQ ID NO 3
<211> LENGTH: 18
<212> TYPE: DNA
<213> ORGANISM: Artificial Sequence
<220> FEATURE:
<223> OTHER INFORMATION: A synthetic primer

<400> SEQUENCE: 3
cacgacgggg agtcaggc                                                18

<210> SEQ ID NO 4
<211> LENGTH: 23
<212> TYPE: DNA
<213> ORGANISM: Artificial Sequence
<220> FEATURE:
<223> OTHER INFORMATION: A synthetic primer

<400> SEQUENCE: 4
gtagcggtgg ttttttttgtt tgc                                         23

<210> SEQ ID NO 5
<211> LENGTH: 50
<212> TYPE: PRT
<213> ORGANISM: Artificial Sequence
<220> FEATURE:
<223> OTHER INFORMATION: A synthetic oligopeptide

<400> SEQUENCE: 5

Gly Arg Gly Arg Gly Arg Gly Arg Gly Arg Gly Gly Arg Pro Gly
```

```
          1               5                  10                 15
Ala Pro Gly Gly Ser Gly Ser Gly Pro Arg His Arg Asp Gly Val Arg
                    20                  25                  30
Arg Pro Gln Lys Arg Pro Ser Cys Ile Gly Cys Lys Gly Thr His Gly
            35                  40                  45
Gly Thr
    50

<210> SEQ ID NO 6
<211> LENGTH: 30
<212> TYPE: PRT
<213> ORGANISM: Artificial Sequence
<220> FEATURE:
<223> OTHER INFORMATION: A synthetic oligopeptide

<400> SEQUENCE: 6

Ser Gly Ser Gly Pro Arg His Arg Asp Gly Val Arg Pro Gln Lys
  1               5                  10                  15
Arg Pro Ser Cys Ile Gly Cys Lys Gly Thr His Gly Gly Thr
            20                  25                  30

<210> SEQ ID NO 7
<211> LENGTH: 21
<212> TYPE: DNA
<213> ORGANISM: Artificial Sequence
<220> FEATURE:
<223> OTHER INFORMATION: A synthetic primer

<400> SEQUENCE: 7
tcttcagcca ctgcccttgt g                                          21

<210> SEQ ID NO 8
<211> LENGTH: 158
<212> TYPE: DNA
<213> ORGANISM: Artificial Sequence
<220> FEATURE:
<223> OTHER INFORMATION: A synthetic oligonucleotide

<400> SEQUENCE: 8
gatatcgctg ttccttagga ccctttact aaccctaatt cgatagcata tgcttcccgt    60
tgggtaacat atgctattga attagggtta gtctggatag tatatactac tacccgggaa  120
gcatatgcta cccgtttagg gttaacaagc ttgatatc                          158

<210> SEQ ID NO 9
<211> LENGTH: 143
<212> TYPE: DNA
<213> ORGANISM: Artificial Sequence
<220> FEATURE:
<223> OTHER INFORMATION: A synthetic oligonucleotide

<400> SEQUENCE: 9
gccggcgatc gatctaaccc taattcgata gtatatacta ctacccggga agcatatgct   60
accgaattag ggttactagc gatagtatat actactaccc gggaagcata tgctaccgaa  120
ttagggttag atcgatcact agt                                          143

<210> SEQ ID NO 10
<211> LENGTH: 147
<212> TYPE: DNA
<213> ORGANISM: Artificial Sequence
<220> FEATURE:
<223> OTHER INFORMATION: A synthetic oligonucleotide
```

```
<400> SEQUENCE: 10
gctgttcctt aggacccttt tactaaccct aattcgatag catatgcttc ccgttgggta        60
acatatgcta ttgaattagg gttagtctgg atagtatata ctactacccg ggaagcatat       120
gctacccgtt tagggttaac aagcttg                                           147

<210> SEQ ID NO 11
<211> LENGTH: 148
<212> TYPE: DNA
<213> ORGANISM: Artificial Sequence
<220> FEATURE:
<223> OTHER INFORMATION: A synthetic oligonucleotide

<400> SEQUENCE: 11
gcgggatagc gtgcgctacc ggatggcggg taatacatgc tatccttaca ttttggcatt        60
ttgggcagct gggaggcggc ggatgggggt gcttcttttc gcacggtgta tgtttgggga      120
cccgcatgcc ggtactggga taggcgca                                         148

<210> SEQ ID NO 12
<211> LENGTH: 16
<212> TYPE: DNA
<213> ORGANISM: Artificial Sequence
<220> FEATURE:
<223> OTHER INFORMATION: A synthetic oligonucleotide

<400> SEQUENCE: 12
gatagcatat gctatc                                                       16

<210> SEQ ID NO 13
<211> LENGTH: 16
<212> TYPE: DNA
<213> ORGANISM: Artificial Sequence
<220> FEATURE:
<223> OTHER INFORMATION: A synthetic oligonucleotide

<400> SEQUENCE: 13
ggaaatacgt cctacc                                                       16

<210> SEQ ID NO 14
<211> LENGTH: 16
<212> TYPE: DNA
<213> ORGANISM: Artificial Sequence
<220> FEATURE:
<223> OTHER INFORMATION: A synthetic oligonucleotide

<400> SEQUENCE: 14
gatagcatat gcttcc                                                       16

<210> SEQ ID NO 15
<211> LENGTH: 16
<212> TYPE: DNA
<213> ORGANISM: Artificial Sequence
<220> FEATURE:
<223> OTHER INFORMATION: A synthetic oligonucleotide

<400> SEQUENCE: 15
ggtaacatat gctatt                                                       16

<210> SEQ ID NO 16
<211> LENGTH: 14
<212> TYPE: DNA
<213> ORGANISM: Artificial Sequence
<220> FEATURE:
<223> OTHER INFORMATION: A synthetic oligonucleotide
```

```
<400> SEQUENCE: 16
ggatagtata tact                                              14

<210> SEQ ID NO 17
<211> LENGTH: 16
<212> TYPE: DNA
<213> ORGANISM: Artificial Sequence
<220> FEATURE:
<223> OTHER INFORMATION: A synthetic oligonucleotide

<400> SEQUENCE: 17
ggaagcatat gctacc                                            16

<210> SEQ ID NO 18
<211> LENGTH: 16
<212> TYPE: DNA
<213> ORGANISM: Artificial Sequence
<220> FEATURE:
<223> OTHER INFORMATION: A synthetic oligonucleotide

<400> SEQUENCE: 18
ggtaatacat gctatc                                            16

<210> SEQ ID NO 19

<400> SEQUENCE: 19

000

<210> SEQ ID NO 20
<211> LENGTH: 16
<212> TYPE: DNA
<213> ORGANISM: Artificial Sequence
<220> FEATURE:
<223> OTHER INFORMATION: A synthetic oligonucleotide
<220> FEATURE:
<221> NAME/KEY: misc_feature
<222> LOCATION: 2,5
<223> OTHER INFORMATION: n = G or A
<220> FEATURE:
<221> NAME/KEY: misc_feature
<222> LOCATION: 3
<223> OTHER INFORMATION: n = T or A
<220> FEATURE:
<221> NAME/KEY: misc_feature
<222> LOCATION: 6,8
<223> OTHER INFORMATION: n = T or C
<220> FEATURE:
<221> NAME/KEY: misc_feature
<222> LOCATION: 9
<223> OTHER INFORMATION: n = A or G
<220> FEATURE:
<221> NAME/KEY: misc_feature
<222> LOCATION: 11
<223> OTHER INFORMATION: n = A, G or C
<220> FEATURE:
<221> NAME/KEY: misc_feature
<222> LOCATION: (15)...(16)
<223> OTHER INFORMATION: n = C or T

<400> SEQUENCE: 20
gnnannannt nctann                                            16

<210> SEQ ID NO 21
<211> LENGTH: 16
<212> TYPE: DNA
<213> ORGANISM: Artificial Sequence
<220> FEATURE:
<223> OTHER INFORMATION: A synthetic oligonucleotide
```

```
<400> SEQUENCE: 21
gatagtatat actact                                                       16

<210> SEQ ID NO 22
<211> LENGTH: 16
<212> TYPE: DNA
<213> ORGANISM: Artificial Sequence
<220> FEATURE:
<223> OTHER INFORMATION: A synthetic oligonucleotide

<400> SEQUENCE: 22
ggaagcatat gctacc                                                       16

<210> SEQ ID NO 23
<211> LENGTH: 16
<212> TYPE: DNA
<213> ORGANISM: Artificial Sequence
<220> FEATURE:
<223> OTHER INFORMATION: A synthetic oligonucleotide

<400> SEQUENCE: 23
gatagcatat gctacc                                                       16

<210> SEQ ID NO 24
<211> LENGTH: 16
<212> TYPE: DNA
<213> ORGANISM: Artificial Sequence
<220> FEATURE:
<223> OTHER INFORMATION: A synthetic oligonucleotide

<400> SEQUENCE: 24
ggaaatacgt cctacc                                                       16

<210> SEQ ID NO 25
<211> LENGTH: 16
<212> TYPE: DNA
<213> ORGANISM: Artificial Sequence
<220> FEATURE:
<223> OTHER INFORMATION: A synthetic oligonucleotide

<400> SEQUENCE: 25
ggtaatacat gctatc                                                       16

<210> SEQ ID NO 26
<211> LENGTH: 15
<212> TYPE: DNA
<213> ORGANISM: Artificial Sequence
<220> FEATURE:
<223> OTHER INFORMATION: A synthetic oligonucleotide
<220> FEATURE:
<221> NAME/KEY: misc_feature
<222> LOCATION: 3, 6,12
<223> OTHER INFORMATION: n = A or G
<220> FEATURE:
<221> NAME/KEY: misc_feature
<222> LOCATION: 4
<223> OTHER INFORMATION: n = A, C or T
<220> FEATURE:
<221> NAME/KEY: misc_feature
<222> LOCATION: 7,9,11,14
<223> OTHER INFORMATION: n = C or T
<220> FEATURE:
<221> NAME/KEY: misc_feature
<222> LOCATION: 8
<223> OTHER INFORMATION: n = A or C
<220> FEATURE:
<221> NAME/KEY: misc_feature
<222> LOCATION: 10,15
```

```
<223> OTHER INFORMATION: n = A, G or T

<400> SEQUENCE: 26
ggnnannnnn nncnn                                                    15

<210> SEQ ID NO 27
<211> LENGTH: 16
<212> TYPE: DNA
<213> ORGANISM: Artificial Sequence
<220> FEATURE:
<223> OTHER INFORMATION: A synthetic oligonucleotide
<220> FEATURE:
<221> NAME/KEY: misc_feature
<222> LOCATION: 3,6,12
<223> OTHER INFORMATION: n = A or G
<220> FEATURE:
<221> NAME/KEY: misc_feature
<222> LOCATION: 4
<223> OTHER INFORMATION: n = A, C or T
<220> FEATURE:
<221> NAME/KEY: misc_feature
<222> LOCATION: 7,9,11,14,16
<223> OTHER INFORMATION: n = C or T
<220> FEATURE:
<221> NAME/KEY: misc_feature
<222> LOCATION: 8
<223> OTHER INFORMATION: n = A or C
<220> FEATURE:
<221> NAME/KEY: misc_feature
<222> LOCATION: 10,15
<223> OTHER INFORMATION: n = A, G or T

<400> SEQUENCE: 27
ggnnannnnn nncnnn                                                   16

<210> SEQ ID NO 28
<211> LENGTH: 17
<212> TYPE: DNA
<213> ORGANISM: Artificial Sequence
<220> FEATURE:
<223> OTHER INFORMATION: A synthetic oligonucleotide
<220> FEATURE:
<221> NAME/KEY: misc_feature
<222> LOCATION: 2,5,11
<223> OTHER INFORMATION: n = A or G
<220> FEATURE:
<221> NAME/KEY: misc_feature
<222> LOCATION: 3
<223> OTHER INFORMATION: n = A, C or T
<220> FEATURE:
<221> NAME/KEY: misc_feature
<222> LOCATION: 6,8,10,13,15
<223> OTHER INFORMATION: n = C or T
<220> FEATURE:
<221> NAME/KEY: misc_feature
<222> LOCATION: 7
<223> OTHER INFORMATION: n = A or C
<220> FEATURE:
<221> NAME/KEY: misc_feature
<222> LOCATION: 9,14
<223> OTHER INFORMATION: n = A or G or T

<400> SEQUENCE: 28
gnnannnnnn ncnnncc                                                  17

<210> SEQ ID NO 29
<211> LENGTH: 18
<212> TYPE: DNA
<213> ORGANISM: Artificial Sequence
<220> FEATURE:
<223> OTHER INFORMATION: A synthetic oligonucleotide
<220> FEATURE:
<221> NAME/KEY: misc_feature
```

```
<222> LOCATION: 3,6,13
<223> OTHER INFORMATION: n = A or G
<220> FEATURE:
<221> NAME/KEY: misc_feature
<222> LOCATION: 4
<223> OTHER INFORMATION: n = A, C or T
<220> FEATURE:
<221> NAME/KEY: misc_feature
<222> LOCATION: 7,10,12,14,15
<223> OTHER INFORMATION: n = C or T
<220> FEATURE:
<221> NAME/KEY: misc_difference
<222> LOCATION: 8
<223> OTHER INFORMATION: n = A, C or G
<220> FEATURE:
<221> NAME/KEY: misc_feature
<222> LOCATION: 9
<223> OTHER INFORMATION: n = A or C
<220> FEATURE:
<221> NAME/KEY: misc_feature
<222> LOCATION: (11)...(11)
<223> OTHER INFORMATION: n = A, G or T
<220> FEATURE:
<221> NAME/KEY: misc_feature
<222> LOCATION: (16)...(16)
<223> OTHER INFORMATION: n = A, G, T or C

<400> SEQUENCE: 29
ggnnannnnn nnnnnntc                                                18

<210> SEQ ID NO 30
<211> LENGTH: 10
<212> TYPE: DNA
<213> ORGANISM: Artificial Sequence
<220> FEATURE:
<223> OTHER INFORMATION: A synthetic oligonucleotide
<220> FEATURE:
<221> NAME/KEY: misc_feature
<222> LOCATION: 1
<223> OTHER INFORMATION: n = A, T, C or G
<220> FEATURE:
<221> NAME/KEY: misc_feature
<222> LOCATION: 4
<223> OTHER INFORMATION: n = A or G
<220> FEATURE:
<221> NAME/KEY: misc_feature
<222> LOCATION: 8
<223> OTHER INFORMATION: n = C or T
<220> FEATURE:
<221> NAME/KEY: misc_feature
<222> LOCATION: 9
<223> OTHER INFORMATION: n = A or C

<400> SEQUENCE: 30 nggntagnnt                                                         10

<210> SEQ ID NO 31
<211> LENGTH: 10
<212> TYPE: DNA
<213> ORGANISM: Artificial Sequence
<220> FEATURE:
<223> OTHER INFORMATION: A synthetic oligonucleotide
<220> FEATURE:
<221> NAME/KEY: misc_feature
<222> LOCATION: 1
<223> OTHER INFORMATION: n = T, C or G
<220> FEATURE:
<221> NAME/KEY: misc_feature
<222> LOCATION: 2
<223> OTHER INFORMATION: n = C, G or T
<220> FEATURE:
<221> NAME/KEY: misc_feature
<222> LOCATION: 3,7
<223> OTHER INFORMATION: n = G or A
<220> FEATURE:
```

```
<221> NAME/KEY: misc_feature
<222> LOCATION: 4
<223> OTHER INFORMATION: n = A or G
<220> FEATURE:
<221> NAME/KEY: misc_feature
<222> LOCATION: 5
<223> OTHER INFORMATION: n = A or T
<220> FEATURE:
<221> NAME/KEY: misc_feature
<222> LOCATION: (8)...(8)
<223> OTHER INFORMATION: n = C or T

<400> SEQUENCE: 31 nnnnnannat                                                               10

<210> SEQ ID NO 32
<211> LENGTH: 10
<212> TYPE: DNA
<213> ORGANISM: Artificial Sequence
<220> FEATURE:
<223> OTHER INFORMATION: A synthetic oligonucleotide
<220> FEATURE:
<221> NAME/KEY: misc_feature
<222> LOCATION: 1
<223> OTHER INFORMATION: n = T, G or C
<220> FEATURE:
<221> NAME/KEY: misc_feature
<222> LOCATION: 2
<223> OTHER INFORMATION: n = G, T or A
<220> FEATURE:
<221> NAME/KEY: misc_feature
<222> LOCATION: 3,7
<223> OTHER INFORMATION: n = G or A
<220> FEATURE:
<221> NAME/KEY: misc_feature
<222> LOCATION: 4
<223> OTHER INFORMATION: n = A or G
<220> FEATURE:
<221> NAME/KEY: misc_feature
<222> LOCATION: 5
<223> OTHER INFORMATION: n = C or T
<220> FEATURE:
<221> NAME/KEY: misc_feature
<222> LOCATION: (8)...(8)
<223> OTHER INFORMATION: n = C, T or G
<220> FEATURE:
<221> NAME/KEY: misc_feature
<222> LOCATION: (9)...(9)
<223> OTHER INFORMATION: n = A or C
<220> FEATURE:
<221> NAME/KEY: misc_feature
<222> LOCATION: (10)...(10)
<223> OTHER INFORMATION: n = T, C or G

<400> SEQUENCE: 32 nnnnnannnn                                                               10

<210> SEQ ID NO 33
<211> LENGTH: 11
<212> TYPE: DNA
<213> ORGANISM: Artificial Sequence
<220> FEATURE:
<223> OTHER INFORMATION: A synthetic oligonucleotide
<220> FEATURE:
<221> NAME/KEY: misc_feature
<222> LOCATION: 1
<223> OTHER INFORMATION: n = A or T
<220> FEATURE:
<221> NAME/KEY: misc_feature
<222> LOCATION: 2
<223> OTHER INFORMATION: n = C or G
<220> FEATURE:
<221> NAME/KEY: misc_feature
<222> LOCATION: 9
<223> OTHER INFORMATION: n = A, T, G or C
```

```
<220> FEATURE:
<221> NAME/KEY: misc_feature
<222> LOCATION: 10
<223> OTHER INFORMATION: n = T, A or C

<400> SEQUENCE: 33
nngatagcnn g                                                              11

<210> SEQ ID NO 34
<211> LENGTH: 16
<212> TYPE: DNA
<213> ORGANISM: Artificial Sequence
<220> FEATURE:
<223> OTHER INFORMATION: A synthetic oligonucleotide
<220> FEATURE:
<221> NAME/KEY: misc_feature
<222> LOCATION: 2
<223> OTHER INFORMATION: n = G or A
<220> FEATURE:
<221> NAME/KEY: misc_feature
<222> LOCATION: 3
<223> OTHER INFORMATION: n = A, T or C
<220> FEATURE:
<221> NAME/KEY: misc_feature
<222> LOCATION: 5,11
<223> OTHER INFORMATION: n = A, G or C
<220> FEATURE:
<221> NAME/KEY: misc_feature
<222> LOCATION: (6)...(10)
<223> OTHER INFORMATION: n = A, T, G or C
<220> FEATURE:
<221> NAME/KEY: misc_feature
<222> LOCATION: 12,15,16
<223> OTHER INFORMATION: n = T or C
<220> FEATURE:
<221> NAME/KEY: misc_feature
<222> LOCATION: (14)...(14)
<223> OTHER INFORMATION: n = A, T or G

<400> SEQUENCE: 34
gnnannnnnn nntnnn                                                         16

<210> SEQ ID NO 35
<211> LENGTH: 1129
<212> TYPE: PRT
<213> ORGANISM: Herpes virus

<400> SEQUENCE: 35
```

Met Ala Pro Pro Gly Met Arg Leu Arg Ser Gly Arg Ser Thr Gly Ala
 1               5                  10                  15

Pro Leu Thr Arg Gly Ser Cys Arg Lys Arg Asn Arg Ser Pro Glu Arg
                20                  25                  30

Cys Asp Leu Gly Asp Asp Leu His Leu Gln Pro Arg Arg Lys His Val
            35                  40                  45

Ala Asp Ser Val Asp Gly Arg Glu Cys Gly Pro His Thr Leu Pro Ile
        50                  55                  60

Pro Gly Ser Pro Thr Val Phe Thr Ser Gly Leu Pro Ala Phe Val Ser
65                  70                  75                  80

Ser Pro Thr Leu Pro Val Ala Pro Ile Pro Ser Pro Ala Pro Ala Thr
                85                  90                  95

Pro Leu Pro Pro Pro Ala Leu Leu Pro Pro Val Thr Thr Ser Ser Ser
               100                 105                 110

Pro Ile Pro Pro Ser His Pro Val Ser Pro Gly Thr Thr Asp Thr His
           115                 120                 125

Ser Pro Ser Pro Ala Leu Pro Pro Thr Gln Ser Pro Glu Ser Ser Gln
       130                 135                 140

```
Arg Pro Pro Leu Ser Ser Pro Thr Gly Arg Pro Asp Ser Ser Thr Pro
145                 150                 155                 160

Met Arg Pro Pro Pro Ser Gln Gln Thr Thr Pro Pro His Ser Pro Thr
                165                 170                 175

Thr Pro Pro Pro Glu Pro Pro Ser Lys Ser Ser Pro Asp Ser Leu Ala
            180                 185                 190

Pro Ser Thr Leu Arg Ser Leu Arg Lys Arg Arg Leu Ser Ser Pro Gln
            195                 200                 205

Gly Pro Ser Thr Leu Asn Pro Ile Cys Gln Ser Pro Pro Val Ser Pro
        210                 215                 220

Pro Arg Cys Asp Phe Ala Asn Arg Ser Val Tyr Pro Pro Trp Ala Thr
225                 230                 235                 240

Glu Ser Pro Ile Tyr Val Gly Ser Ser Ser Asp Gly Asp Thr Pro Pro
                245                 250                 255

Arg Gln Pro Pro Thr Ser Pro Ile Ser Ile Gly Ser Ser Ser Pro Ser
            260                 265                 270

Glu Gly Ser Trp Gly Asp Asp Thr Ala Met Leu Val Leu Leu Ala Glu
        275                 280                 285

Ile Ala Glu Glu Ala Ser Lys Asn Glu Lys Glu Cys Ser Glu Asn Asn
290                 295                 300

Gln Ala Gly Glu Asp Asn Gly Asp Asn Glu Ile Ser Lys Glu Ser Gln
305                 310                 315                 320

Val Asp Lys Asp Asp Asn Asp Asn Lys Asp Asp Glu Glu Gln Glu
                325                 330                 335

Thr Asp Glu Glu Asp Glu Glu Asp Glu Glu Asp Asp Glu Glu Asp
            340                 345                 350

Asp Glu Glu Asp Asp Glu Glu Asp Asp Glu Glu Asp Asp Glu Glu Asp
            355                 360                 365

Asp Glu Glu Glu Asp Glu Glu Glu Asp Glu Glu Asp Glu Glu Glu
            370                 375                 380

Asp Glu Glu Glu Glu Glu Asp Glu Glu Asp Asp Asp Asp Glu Asp Asn
385                 390                 395                 400

Glu Asp Glu Glu Asp Asp Glu Glu Asp Lys Lys Glu Asp Glu Glu
                405                 410                 415

Asp Gly Gly Asp Gly Asn Lys Thr Leu Ser Ile Gln Ser Ser Gln Gln
            420                 425                 430

Gln Gln Glu Pro Gln Gln Gln Glu Pro Gln Gln Glu Pro Gln Gln
            435                 440                 445

Gln Glu Pro Gln Gln Gln Glu Pro Gln Gln Gln Glu Pro Gln Gln Gln
            450                 455                 460

Glu Pro Gln Gln Gln Glu Pro Gln Gln Arg Glu Pro Gln Gln Arg Glu
465                 470                 475                 480

Pro Gln Gln Arg Glu Pro Gln Gln Arg Glu Pro Gln Gln Arg Glu Pro
            485                 490                 495

Gln Gln Arg Glu Pro Gln Gln Arg Glu Pro Gln Gln Arg Glu Pro Gln
            500                 505                 510

Gln Arg Glu Pro Gln Gln Arg Glu Pro Gln Gln Arg Glu Pro Gln Gln
            515                 520                 525

Arg Glu Pro Gln Gln Glu Pro Gln Gln Glu Pro Gln Gln Gln
            530                 535                 540

Glu Pro Gln Gln Gln Glu Pro Gln Gln Glu Pro Gln Gln Gln Glu
545                 550                 555                 560
```

-continued

```
Pro Gln Gln Gln Glu Pro Gln Gln Gln Glu Pro Gln Gln Gln Glu Pro
                565                 570                 575
Gln Gln Gln Glu Pro Gln Gln Gln Glu Pro Gln Gln Gln Glu Pro Gln
                580                 585                 590
Gln Gln Asp Glu Gln Gln Gln Asp Glu Gln Gln Gln Asp Glu Gln Gln
                595                 600                 605
Gln Asp Glu Gln Gln Gln Asp Glu Gln Gln Gln Asp Glu Gln Gln Gln
                610                 615                 620
Asp Glu Gln Gln Gln Asp Glu Gln Gln Gln Asp Glu Gln Gln Gln Gln
625                 630                 635                 640
Asp Glu Gln Gln Gln Gln Asp Glu Gln Gln Gln Gln Glu Glu Gln Glu
                645                 650                 655
Gln Gln Glu Glu Gln Gln Gln Asp Glu Gln Gln Gln Asp Glu Gln Gln
                660                 665                 670
Gln Asp Glu Gln Gln Gln Asp Glu Gln Gln Gln Asp Glu Gln Gln Gln
                675                 680                 685
Gln Asp Glu Gln Gln Gln Asp Glu Gln Gln Gln Glu Glu Gln Glu Glu
                690                 695                 700
Glu Gln Glu Glu Glu Glu Gln Glu Glu Glu Glu Gln Glu Glu Glu Glu
705                 710                 715                 720
Glu Gln Glu Glu Glu Leu Glu Glu Gln Glu Glu Leu Glu Glu Gln Glu
                725                 730                 735
Glu Gln Glu Leu Glu Glu Gln Glu Glu Leu Glu Glu Gln Glu Glu Gln
                740                 745                 750
Glu Leu Glu Glu Gln Glu Glu Leu Glu Glu Gln Glu Glu Gln Glu Leu
                755                 760                 765
Glu Glu Gln Glu Gln Glu Leu Glu Glu Gln Glu Gln Glu Leu Glu Glu
                770                 775                 780
Gln Glu Gln Glu Leu Glu Glu Gln Glu Gln Glu Leu Glu Glu Gln Glu
785                 790                 795                 800
Gln Glu Leu Glu Glu Gln Glu Gln Glu Leu Glu Glu Gln Glu Gln Glu
                805                 810                 815
Leu Glu Glu Gln Glu Gln Glu Gln Glu Leu Glu Glu Val Glu Glu Gln
                820                 825                 830
Glu Gln Glu Gln Glu Gln Glu Gln Glu Leu Glu Glu Val Glu Glu Gln
                835                 840                 845
Gln Glu Gln Glu Gln Glu Gln Glu Gln Glu Leu Glu Glu Val Glu Glu
                850                 855                 860
Gln Glu Glu Gln Glu Leu Glu Glu Val Glu Glu Gln Glu Glu Gln Glu
865                 870                 875                 880
Leu Glu Glu Val Glu Glu Gln Glu Gln Gln Gly Val Glu Gln Gln Glu
                885                 890                 895
Gln Glu Thr Val Glu Glu Pro Ile Ile Leu His Gly Ser Ser Ser Glu
                900                 905                 910
Asp Glu Met Glu Val Asp Tyr Pro Val Val Ser Thr His Glu Gln Ile
                915                 920                 925
Ala Ser Ser Pro Pro Gly Asp Asn Thr Pro Asp Asp Pro Gln Pro
                930                 935                 940
Gly Pro Ser Arg Glu Tyr Arg Tyr Val Leu Arg Thr Ser Pro Pro His
945                 950                 955                 960
Arg Pro Gly Val Arg Met Arg Arg Val Pro Val Thr His Pro Lys Lys
                965                 970                 975
Pro His Pro Arg Tyr Gln Gln Pro Pro Val Pro Tyr Arg Gln Ile Asp
```

```
            980             985             990
Asp Cys Pro Ala Lys Ala Arg Pro Gln His Ile Phe Tyr Arg Arg Phe
        995             1000            1005

Leu Gly Lys Asp Gly Arg Arg Asp Pro Lys Cys Gln Trp Lys Phe Ala
    1010            1015            1020

Val Ile Phe Trp Gly Asn Asp Pro Tyr Gly Leu Lys Lys Leu Ser Gln
1025            1030            1035            1040

Ala Phe Gln Phe Gly Gly Val Lys Ala Gly Pro Val Ser Cys Leu Pro
            1045            1050            1055

His Pro Gly Pro Asp Gln Ser Pro Ile Thr Tyr Cys Val Tyr Val Tyr
        1060            1065            1070

Cys Gln Asn Lys Asp Thr Ser Lys Lys Val Gln Met Ala Arg Leu Ala
        1075            1080            1085

Trp Glu Ala Ser His Pro Leu Ala Gly Asn Leu Gln Ser Ser Ile Val
            1090            1095            1100

Lys Phe Lys Lys Pro Leu Pro Leu Thr Gln Pro Gly Glu Asn Gln Gly
1105            1110            1115            1120

Pro Gly Asp Ser Pro Gln Glu Met Thr
            1125

<210> SEQ ID NO 36
<211> LENGTH: 152
<212> TYPE: DNA
<213> ORGANISM: Artificial Sequence
<220> FEATURE:
<223> OTHER INFORMATION: A synthetic oligonucleotide

<400> SEQUENCE: 36
gccggcgatc gatctaaccc taattcgata gcatatgctt cccgttgggt aacatatgct      60
attgaattag ggttagtctg gatagtatat actactaccc gggaagcata tgctacccgt     120
ttagggttag ggttaggaga tcgatcacta gt                                   152

<210> SEQ ID NO 37
<211> LENGTH: 152
<212> TYPE: DNA
<213> ORGANISM: Artificial Sequence
<220> FEATURE:
<223> OTHER INFORMATION: A synthetic oligonucleotide

<400> SEQUENCE: 37
gccggcgatc gatctaaccc taattcgata gcatatgcta ccacccggat agcatatgct      60
accgaattag ggttactagc gatagcatat gctaccaccc ggatagcata tgctaccgaa     120
ttagggttag ggttaggaga tcgatcacta gt                                   152

<210> SEQ ID NO 38
<211> LENGTH: 159
<212> TYPE: DNA
<213> ORGANISM: Artificial Sequence
<220> FEATURE:
<223> OTHER INFORMATION: A synthetic oligonucleotide

<400> SEQUENCE: 38
gccggcgatc gatcctaacc ctaaccctaa ttcgatagca tatgcttccc gttgggtaac      60
atatgctatt gaattagggt tagtctggat agtatatact actacccggg aagcatatgc     120
tacccgttta gggttagggt taggagatcg atcactagt                            159

<210> SEQ ID NO 39
```

```
<211> LENGTH: 159
<212> TYPE: DNA
<213> ORGANISM: Artificial Sequence
<220> FEATURE:
<223> OTHER INFORMATION: A synthetic oligonucleotide

<400> SEQUENCE: 39
gccggcgatc gatcctaacc ctaaccctaa ttcgatagca tatgctacca cccggatagc      60
atatgctacc gaattagggt tactagcgat agcatatgct accacccgga tagcatatgc     120
taccgaatta gggttagggt taggagatcg atcactagt                            159

<210> SEQ ID NO 40
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 40
gccggcatgc tagcatacta gt                                               22

<210> SEQ ID NO 41
<211> LENGTH: 119
<212> TYPE: DNA
<213> ORGANISM: Artificial Sequence
<220> FEATURE:
<223> OTHER INFORMATION: A synthetic oligonucleotide

<400> SEQUENCE: 41
gccggcgatc gatcgatagt atatactact acccgggaag catatgctac cgatcgatca      60
ctagcatcga tagtatatac tactacccgg gaagcatatg ctaccgatcg atcactagt     119

<210> SEQ ID NO 42
<211> LENGTH: 16
<212> TYPE: DNA
<213> ORGANISM: Artificial Sequence
<220> FEATURE:
<223> OTHER INFORMATION: A synthetic oligonucleotide

<400> SEQUENCE: 42
gatagtatat actact                                                      16

<210> SEQ ID NO 43
<211> LENGTH: 16
<212> TYPE: DNA
<213> ORGANISM: Artificial Sequence
<220> FEATURE:
<223> OTHER INFORMATION: A synthetic oligonucleotide

<400> SEQUENCE: 43
gatagcatat gctacc                                                      16

<210> SEQ ID NO 44
<211> LENGTH: 16
<212> TYPE: DNA
<213> ORGANISM: Artificial Sequence
<220> FEATURE:
<223> OTHER INFORMATION: A synthetic oligonucleotide

<400> SEQUENCE: 44
ggaaatacgt cctacc                                                      16

<210> SEQ ID NO 45
<211> LENGTH: 16
```

```
<212> TYPE: DNA
<213> ORGANISM: Artificial Sequence
<220> FEATURE:
<223> OTHER INFORMATION: A synthetic oligonucleotide

<400> SEQUENCE: 45
ggtaatacat gctatc                                                      16

<210> SEQ ID NO 46
<211> LENGTH: 16
<212> TYPE: DNA
<213> ORGANISM: Artificial Sequence
<220> FEATURE:
<223> OTHER INFORMATION: A synthetic oligonucleotide

<400> SEQUENCE: 46
ggaagcatat gctacc                                                      16
```

EFFICIENT *ORIP*/EBNA-1 PLASMID VECTOR

CROSS-REFERENCE TO RELATED APPLICATIONS

The application claims the benefit of the filing date of U.S. application Ser. No. 61/020,918, filed on Jan. 14, 2008, the disclosure of which is incorporated by reference herein.

STATEMENT OF GOVERNMENT RIGHTS

The invention was made with a grant from the Government of the United States of America (grant CA022443 from the National Institutes of Health). The Government has certain rights in the invention.

BACKGROUND

The requirements in cis for DNA to serve as an origin of DNA synthesis, that is, an initiator, in metazoan cells are not well defined. Experimental findings have indicated there may be no requirements under some conditions (Harland and Laskey, 1980) while other findings have mapped an origin to specific nucleotides (Abdurashidova, 2000), a result consistent with a specific DNA sequence contributing to an origin of synthesis. The Epstein-Barr Viral (EBV) origin of plasmid DNA synthesis, oriP, efficiently supports licensed DNA synthesis in a variety of higher eukaryotic cells. This origin uses only one viral protein, EBNA-1, while all other factors are provided by the cell. It thus serves as one model for characterizing cis-acting requirements for a licensed, metazoan origin of DNA synthesis.

The origin of DNA synthesis within oriP is the Dyad Symmetry (DS) element, which has been genetically dissected to identify several of its key features. DS is composed of two pairs of binding sites for its only required viral protein EBNA-1, three 9 bp elements that resemble the telomeric repeats of the ends of human chromosomes and are half-binding sites for TTAGGG-repeat Binding Factor 2 (TRF2), a dyad element from which the name was derived, and a region upstream of DS that was found to be helically unstable (Baer et al., 1984; Bashaw and Yates, 2001; Deng et al., 2002; Niller et al., 1985; Polonskaya et al., 2004; Rawlins et al., 1985; Yates et al., 2000). Of these elements, a pair of appropriately spaced EBNA-1-binding sites was found to be the minimal cis-acting element required for the replicative function of DS (Bashaw and Yates, 2001).

The DS element recruits multiple licensing factors for DNA replication (e.g. ORC1-6, MCM2-7, Cdt1, Geminin), which function indistinguishably from the roles assigned to them with human chromosomes (Chaudhuri et al., 2001; Dhar et al., 2001; Julien et al., 2004; Ritzi et al., 2003; Shepers et al., 2001). The DS element recruits these proteins either directly by serving as a substrate for sequence-specific binding, as in the case of TRF2, or indirectly through proteins that bind it site-specifically, and also bind additional proteins. TRF2, for example, can bind ORC1 (Atanasiu et al., 2006). EBNA-1 has an N-terminal domain that is required for the synthesis of oriP and mimics the human HMGA1a protein in both its overall amino acid composition and it's AT-hook sequence motifs (Hung et al., 2001; Sears et al., 2004). This molecular mimicry has been demonstrated by the finding that HMGA1a fused to the DNA-binding and dimerization domain of EBNA-1 restores the ability to support DNA synthesis to this derivative of EBNA-1 (Hung et al., 2001; Sears et al., 2004; Altman et al., 2006). These experiments showed that the N-terminal domain of EBNA-1 and HMGA1a both confer origin function to DS when bound by it site-specifically.

EBV has a second plasmid origin of DNA synthesis, Rep*, which has been experimentally compared to DS (Wang et al., 2006). Rep* contains two EBNA-1-binding sites with 21 bp center-to-center spacing, which, as with DS, is critical for pre-replication complex (preRC) recruitment and replicative function (Wang et al., 2006). However, Rep* does not contain a dyad, TRF2-binding sites, nor a helically unstable region upstream of it, indicating that these elements are not essential for the initiation of DNA synthesis and at most may play auxiliary roles in this process (Wang et al., 2006).

SUMMARY OF THE INVENTION

The lack of defined cis-acting elements in mammalian chromosomal origins of DNA synthesis led to the identification of features of DS that contribute to its efficiency of supporting the initiation of DNA synthesis. As described herein, several candidates for EBNA-1-dependent origins of DNA synthesis, modeled upon the evolutionarily-selected arrangement of the cis elements of DS, were prepared. Like DS, these engineered (synthetic) candidates contain four natural (native) EBNA-1-binding sites, but have a wide-range of different affinities for EBNA-1. Derivatives of the engineered candidate origins were also prepared that include TRF2-half-binding sites in the arrangement present in DS because the interaction between TRF2 and EBNA-1 increases the apparent affinity of EBNA-1 for its binding site.

Using these engineered candidate origins, it was found that there was a direct correlation between the affinity of EBNA-1's binding to an origin when TRF2-half-binding sites were present, and the efficiency of initiating DNA synthesis, as well as the efficiency of supporting establishment (maintenance) with that candidate origin. In addition, the presence of half-binding sites for TRF2 flanking the pairs of EBNA-1-binding sites enhanced the synthesis of these candidate origins to a greater extent than could be expected from previous analyses. Origins of DNA synthesis were also prepared that were several-fold more efficient than wild-type DS (wtDS) in their abilities to initiate DNA synthesis and to promote their extrachromosomal establishment, e.g., for at least 6 weeks. These findings indicate that the efficiency of plasmid establishment in part reflects the efficiency of the initiation of DNA synthesis. The findings support a model in which the affinity of EBNA-1 for its origin binding sites differentially affects the structure of the bound DNA and/or EBNA-1 to promote the recruitment of TRF2 and the cellular replicative machinery.

The invention thus provides a recombinant vector that incorporates a DNA sequence having a synthetic origin of DNA synthesis (e.g., a synthetic oriP) that provides a significantly more efficient origin of DNA synthesis, e.g., having an efficiency of at least 1.2, 1.5, 1.7, 1.9, 2.1, times or more, that of a corresponding vector with a wtDS sequence, and which allows at least 2-fold, 4-fold, 6-fold, 8-fold, 10-fold or more colonies to be generated that carry the recombinant vector extrachromosomally, relative to a vector with a wtDS sequence. In one embodiment, a recombinant vector that incorporates a synthetic origin of DNA synthesis has an efficiency of DNA synthesis that is substantially the same as or lower than, e.g., 0.7, 0.8 or 0.9, times that of, or lower colony formation relative to, a corresponding vector with a wtDS sequence. Such a recombinant vector may be useful to transiently express a desirable gene or express a desirable gene at lower levels than a vector that has a more efficient origin of DNA synthesis. In one embodiment, a recombinant vector that incorporates a synthetic origin of DNA synthesis has an enhanced efficiency of DNA synthesis and colony formation (establishment) relative to a corresponding vector with a wtDS sequence. Such a recombinant vector may be useful to enhance long term (stable) expression of a desirable gene or express a desirable gene at higher levels relative to a corresponding vector with wtDS. For example, for cells that are difficult to transform, e.g., stem cells or nondividing cells such as lung cells, the use of recombinant vectors with a synthetic origin of DNA synthesis with an enhanced efficiency of DNA synthesis and/or colony formation provides for enhanced transformation efficiency. The synthetic origin of DNA synthesis binds EBNA-1 and is capable of initiating DNA synthesis of linked sequences and maintaining the linked sequences in a cell. The synthetic origin of DNA synthesis includes at least two binding sites for EBNA-1, e.g., at least two pairs of binding sites for EBNA-1, which EBNA-1 binding sites are flanked by at least two half-binding sites for TRF2 or at least two binding sites for a protein that enhances the affinity of EBNA-1 for the synthetic origin of DNA synthesis.

In one embodiment, the invention provides a recombinant vector comprising a DNA segment having a synthetic origin of DNA synthesis that binds EBNA-1 or a wild-type protein from a lymphotrophic herpes virus which corresponds to EBNA-1 of EBV, e.g., LANA1 of Kaposi's Sarcoma Herpes Virus (see, for instance, NCBI Accession No. YP_001129431, the disclosure of which is incorporated by reference herein). The synthetic origin of DNA synthesis, when present in the vector in a cell that expresses EBNA-1 or a corresponding protein of a lymphotrophic herpes virus, is capable of initiating DNA synthesis of sequences linked to the synthetic origin of DNA synthesis and maintaining the linked sequences. The synthetic origin of DNA synthesis includes at least two binding sites for EBNA-1 or the corresponding protein from a lymphotrophic herpes virus, wherein the two EBNA-1 or corresponding protein binding sites are flanked by at least two half-binding sites for TRF2 or at least two binding sites for a protein that enhances the affinity of EBNA-1 or the corresponding protein for the synthetic origin of DNA synthesis.

The vectors of the invention may be particularly useful for gene therapy, e.g., for transforming embryonic stem cells with, for example, at least one therapeutic gene, for the transfer of large DNA inserts to cells, for preparing libraries, and for preparing embryonic stem cells from adult somatic cells (see Yu et al., "Induced Pluripotent Stem Cell Lines Derived from Human Somatic Cells", Science, published Nov. 20, 2007; Nakagawa et al., Nat. Biotech., "Generation of Induced Pluripotent Stem Cells Without Myc from Mouse and Human Fibroblast", epublished Nov. 30, 2007, and Takahashi et al., Cell, "Induction of Pluripotent Stem Cells from Adult Human Fibroblasts by Defined Factors", epublished Nov. 30, 2007, the disclosures of which are incorporated by reference herein). For instance, pluripotent human stem cells may be prepared from differentiated human somatic cells via introduction of a recombinant vector of the invention which contains and expresses one or a combination of Oct3, Oct4, Sox2, Klf4, C-myc, NANOG, and/or LIN28, e.g., Oct3, Oct4, Sox2, Klf4 and C-myc; Oct3, Oct4, Sox2, and Klf4; or Oct3, Oct4, Sox2, NANOG and LIN28. In one embodiment, a recombinant vector of the invention is employed to deliver a γc gene (a γ chain gene) to autologous bone-marrow derived CD34+ cells ex vivo and those cells introduced to patients with X-linked severe combined immunodeficiency (SCID-X1).

The invention further provides a method to maintain and express at least one heterologous open reading frame in a cell. The method includes contacting a cell with a recombinant plasmid having at least one heterologous open reading frame and a DNA sequence having a synthetic origin of DNA synthesis of the invention. The synthetic origin of DNA synthesis, when present in a cell that expresses EBNA-1, is capable of initiating DNA synthesis of linked sequences and maintaining the linked sequences. The synthetic origin of DNA synthesis includes at least two binding sites for EBNA-1, e.g., at least two pairs of binding sites for EBNA-1, which are flanked by at least two half-binding sites for TRF2 or binding sites for a protein that enhances the affinity of EBNA-1 for the synthetic origin of DNA synthesis. In one embodiment, the cell or the plasmid includes an expression cassette having a DNA segment which encodes EBNA-1, for instance, a derivative of EBNA-1 which has reduced cytotoxicity relative to wild-type EBNA-1, which derivative lacks sequences present in the corresponding wild-type protein which activate transcription from an integrated template, and which derivative activates transcription of the heterologous open reading frame at levels at least 5% that of the corresponding wild-type protein. Also provided is an isolated cell having the recombinant plasmid. In one embodiment, the recombinant vector encodes a γc gene (a γ chain gene) and EBNA-1, and that vector is introduced to autologous bone-marrow derived CD34+ cells ex vivo. Those cells, e.g., after expansion, are introduced to patients with X-linked severe combined immunodeficiency (SCID-X1), e.g., about 1 to $50 \times 10^6$ cells/kg are introduced to a patient. In another embodiment, the recombinant vector encodes a CFTR gene (a γ chain gene) and EBNA-1, and that vector is administered to the lungs or bronchi of a patient with cystic fibrosis. The vectors of the invention may be administered repeatedly over time.

The invention also provides a method to maintain and express at least one heterologous open reading frame in a cell. The method includes contacting a cell with a recombinant plasmid that includes at least one heterologous open reading frame, a DNA sequence having a synthetic origin of DNA synthesis of the invention, and a DNA segment encoding EBNA-1. The plasmid, when present in a cell, is capable of initiating DNA synthesis of linked sequences and maintaining linked sequences. The synthetic origin of DNA synthesis includes at least two binding sites for EBNA-1, e.g., at least two pairs of binding sites for EBNA-1, which are flanked by at least two half-binding sites for TRF2 or binding site for a protein that enhances the affinity of EBNA-1 for the synthetic origin of DNA synthesis. In one embodiment, the vector includes an expression cassette having a DNA segment which encodes a derivative of EBNA-1 which has reduced cytotoxicity relative to wild-type EBNA-1, which derivative lacks sequences present in the corresponding wild-type protein which activate transcription of an integrated template, and which derivative activates transcription of the heterologous open reading frame at levels at least 5% that of the corresponding wild-type protein. Also provided is an isolated cell having the recombinant plasmid.

For instance, the use of a derivative of EBNA-1 which has reduced cytotoxicity relative to wild-type EBNA-1, for example, one that lacks one or more residues between residue 65 and 87, but includes sequences with at least 80%, 85%, 90%, 95% or more, amino acid sequence identity with residues 1 to 40 and 328 to 641 of SEQ ID NO: 1, or includes a nuclear localization sequence and at least three consecutive tripeptides selected from the combination of Gly-Gly-Ala, Gly-Ala-Gly, Gly-Gly-Gly, Ala-Gly-Ala or Ala-Gly-Ala, or at least 80%, 85%, 90%, 95% or more, amino acid sequence identity to SEQ ID NO:1, optionally fused at its N-terminus with a heterologous protein, e.g., HMGA1a, in cells such as stem cells, or in therapeutic methods, may be desirable.

The recombinant vectors of the invention may be administered to a host mammal by any means, e.g., via electroporation, injection or in a complex with lipids. The recombinant vectors of the invention, e.g., those which express EBNA-1 or are present in cells that express EBNA-1, are suitable for readministration, as EBNA-1 is not well recognized by cytotoxic T cells.

The invention provides vectors for use in medical therapy, such as for gene or cell therapy, optionally in conjunction with other compounds. Accordingly, the vectors of the invention are useful to deliver genes to cells ex vivo or in vivo, to correct gene defects, e.g., by introducing a gene encoding a functional gene product, supplement gene expression, or introduce genes useful to inhibit or treat cancer or other proliferative diseases. Also provided is the use of the vectors for the manufacture of a medicament for gene therapy or cell therapy, e.g., to transfer therapeutic or prophylactic gene products.

BRIEF DESCRIPTION OF THE FIGURES

FIG. 6. Exemplary wild-type protein from a lymphotrophic herpes virus which corresponds to EBNA-1 of EBV, e.g., LANA1 of Kaposi's Sarcoma Herpes Virus (SEQ ID NO:35).

DETAILED DESCRIPTION OF THE INVENTION

Figure 1A:
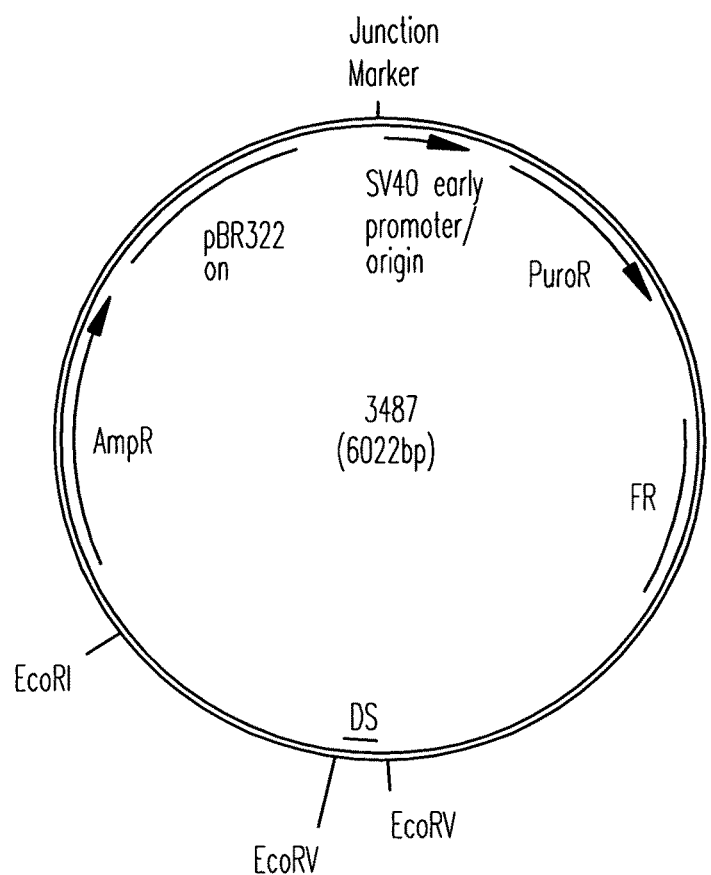
FIG. 1. The oriP plasmid backbone used to introduce the multiple cloning site (MCS) and engineered origins of DNA synthesis. (A) The plasmid p3487 is derived from the pPUR vector from Clontech, which contains a pBR322 origin for plasmid replication in *E. coli* and resistance to both ampicillin and puromycin. The wild-type oriP sequence has been inserted into a unique BamHI restriction site, which was destroyed near FR but was retained near DS. The MCS of plasmid p3488 was inserted between the EcoRV sites flanking DS of p3487. Subsequent insertions of the engineered origins, or the reintroduction of wtDS, were made into unique NgoMIV and SpeI sites present within this MCS of p3488. (B) A graphical representation of each class of origin tested. Within each class, only the sequences corresponding to the EBNA-1-binding sites differ. Plasmids p3487 and p3567, which includes 1.2 kb of lambda phage DNA inserted in the EcoRI site of p3487, contain the wild type DS (wtDS) element between the EcoRV sites as found in the B95-8 strain of EBV (Baer et al., 1984), and serve as positive-control origins. Plasmid p3488 has a 22 bp MCS inserted between the EcoRV sites of p3487 to remove and replace wtDS (MCS-only), and serves as an origin-less negative-control. Test plasmids contain four EBNA-1-binding sites of a range of different affinities in the same arrangement observed in wtDS, in the absence or presence of TRF2-half-binding sites. Two origins (wtDS and 4×FRbs) were further modified to include one or two complete TRF2-binding sites as well. The arrows above the TRF2-binding sites denote the N-to-C terminal orientation that TRF2 would use to bind to these sites as are found in wtDS. All origins were inserted between the NgoMIV and SpeI sites of p3488 to ensure that the only differences between the test plasmids were the origin sequences. The sequences of all origins tested are given in FIG. 2.

The Epstein-Barr virus is a member of the herpes family of viruses. The viral genome is usually maintained as a nuclear plasmid in the cells that it infects. One of the primary latent viral proteins, EBNA-1, binds to a replication origin (oriP) within the viral genome and mediates replication and partitioning of the plasmid during division of the host cell. EBNA-1 is a site-specific DNA binding protein, that binds to clusters of sites in EBV called FR (family of repeats) and DS (dyad symmetry), which together form the about 1 Kbp viral plasmid origin of replication oriP. oriP includes the DS and FR regions. The DS region has four EBNA-1 binding sites, as well as three half-binding sites for the human TRF-2 protein. Interestingly, the FR region has 20 high-affinity binding sites for EBNA-1.

The invention provides improved oriP containing vectors by engineering the cis acting element, e.g., oriP, to yield vectors with synthetic origins of DNA synthesis having, in one embodiment, EBNA-1 binding sites that result in, in one embodiment, enhanced replication and establishment of vector sequences in the presence of EBNA-1. The synthetic origins of DNA synthesis of the invention are synthetic in that the nucleotide sequence in the origin of replication, the number, sequence or arrangement of EBNA-1 (or a corresponding protein, as described herein) binding sites, the number, sequence or arrangement of human TRF2 binding sites or binding sites for a protein that enhances the affinity of EBNA-1 (or the corresponding protein) for the synthetic origin of DNA synthesis, the spacing between EBNA-1 binding sites, or any combination thereof, and also optionally the sequences 5' and/or 3' to the synthetic origin of replication in a vector, is different than that found in wild-type oriP or wild-type EBV (or other lymphotrophic herpes virus), however, the spacing between EBNA-1 binding sites in the synthetic origin of replication (center to center spacing, i.e., from the two-fold axis of one binding site to the two-fold axis of the other binding site) is preferably that found in naturally occurring origins of replication in the herpes family of viruses, e.g., a 21, 24 or 30 bp center to center spacing. Thus, a synthetic origin of DNA synthesis of the invention does not have the sequence of the 4 EBNA-1 binding sites found in wild-type DS, e.g., GCTGTTCCTTAGGACCCTTTTACTAAC-CCTAATTCGATAGCATATGCTTC CCGTTGGGTAA-CATATGCTATTGAATTAGGGTTAGTCTG-GATAGTATATA CTACTACCCGGGAAGCATATGCTACCCGTTTAG GGT-TAACAAGCTTG (SEQ ID NO:10), the sequence of the 20 EBNA-1 binding sites found in wild-type FR, the sequence of the EBNA-1 binding sites found in wild-type Rep*, or the sequence of the EBNA-1 binding sites found in wild-type Site III, e.g., one that includes G CGGGATAGCG TGCGC-TACCG GATGGCGGGT AATACATGCT ATCCTTACAT TTTGGCATTT TGGGCAGCTG GGAGGCGGCG GATGGGGGTG CTTCTTTTCG CACGGTGTAT GTTTGGGGAC CCGCATGCCG GTACTGGGAT AGGCGCA (SEQ ID NO:11) in the context of those sites in EBV.

For instance, synthetic origins of DNA synthesis of the invention may have fewer EBNA-1 binding sites than in wild-type DS, FR, Rep* or Site III but include wild-type EBNA-1 binding sequences (optionally from two or more sources), optionally with the spacing found between EBNA-1 binding sites in wild-type DS, FR, Rep* or Site III; more EBNA-1 binding sites than in wild-type DS, FR, Rep* or Site III but include wild-type EBNA-1 binding sequences (optionally from two or more sources), optionally with the spacing found between EBNA-1 binding sites in wild-type DS, FR, Rep* or Site III; the same number of EBNA-1 binding sites as in wild-type DS, FR, Rep* or Site III but have non-wild-type EBNA-1 binding sequences, optionally with the spacing found between EBNA-1 binding sites in wild-type DS, FR, Rep* or Site III; fewer EBNA-1 binding sites than in wild-type DS, FR, Rep* or Site III which binding sites include non-wild-type EBNA-1 sequences, optionally with the spacing found between EBNA-1 binding sites in wild-type DS, FR, Rep* or Site III; more EBNA-1 binding sites than in wild-type DS, FR, Rep* or Site III which binding sites include non-wild-type EBNA-1 sequences, optionally with the spacing found between EBNA-1 binding sites in wild-type DS, FR, Rep* or Site III; fewer EBNA-1 binding sites than in wild-type DS, FR, Rep* or Site III with a combination of wild-type and non-wild-type EBNA-1 binding sequences, optionally with the spacing found between EBNA-1 binding sites in wild-type DS, FR, Rep* or Site III; more EBNA-1 binding sites than in wild-type DS, FR, Rep* or Site III with a combination of wild-type and non-wild-type EBNA-1 binding sequences, optionally with the spacing found between EBNA-1 binding sites in wild-type DS, FR, Rep* or Site III; or the same number of EBNA-1 binding sites relative to those in wild-type DS, FR, Rep* or Site III with a combination of wild-type and non-wild-type EBNA-1 binding sequences, optionally with the spacing found between EBNA-1 binding sites in wild-type DS, FR, Rep* or Site III. Examples of wild-type EBNA-1 binding sites include but are not limited to those found in wild-type DS, e.g., GATAGCATATGCTTCC, GGTAACATATGCTATT, GGATAGTATATACT, or GGAAGCATATGCTACC (SEQ ID Nos:14-17), wild-type FR, e.g., GATAGCATATGCTATC (SEQ ID NO:12), wild-type Rep*, e.g., GGAAATACGTCCTACC (SEQ ID NO:13), or wild-type Site III, e.g., GGTAATACATGCTATC (SEQ ID NO:18). In one embodiment, the spacing between EBNA-1 binding sites is that found between EBNA-1 binding sites in DS, FR, Rep* or Site III. In one embodiment, the EBNA-1 binding sites in the synthetic origin of DNA synthesis are flanked by at least two half-binding sites for TRF2 or binding sites for a protein that enhances the affinity of EBNA-1 for the synthetic origin of DNA synthesis. For instance, the TRF2 binding sites may be positioned in the vector to be most efficacious for binding of the TRF2/EBNA-1 complex (bringing together 2 half-sites). The two TRF2 half-binding sites, if flanking the two EBNA-1 binding sites, may be in opposite or the same orientation relative to each other. Two TRF2 half-binding sites, if present in tandem, are in the same orientation. In one embodiment, the EBNA-1 binding sites employed in the synthetic origin of DNA synthesis include EBNA-1 binding sites from wild-type FR, and are flanked by two TRF2 half-binding sites.

Using these synthetic origins, a direct correlation was found between the affinity of EBNA-1's binding to an origin and the efficiency of initiating DNA synthesis and of supporting extrachromosomal establishment with that origin when TRF2 half-binding sites were present in cis. The presence of half-binding sites for TRF2 flanking the pairs of EBNA-1 binding sites enhanced the synthesis of these origins to a greater extent than was expected. Moreover, synthetic origins of DNA synthesis were prepared that are several-fold more efficient than wild-type DS in their abilities to initiate DNA synthesis and to promote their extra chromosomal establishment. These findings indicate that the efficiency of plasmid establishment in part reflects the efficiency of the initiation of DNA synthesis.

DEFINITIONS

A "derivative" of EBNA-1 or a corresponding protein in a lymphotropic herpes virus is a protein which is modified relative to a corresponding wild-type protein, i.e., the derivative has a modification which includes a deletion, insertion or substitution, or any combination thereof, of at least one amino acid in a region corresponding to the unique (nonrepetitive) region in LR1, which modification is associated with the lack of substantial transcriptional activation from an integrated template and the reduction in cytotoxicity of the derivative. Like the corresponding wild-type protein, the derivative dimerizes and binds DNA containing a DNA sequence which binds the corresponding wild-type protein with an affinity that is at least 10% that of the binding of a DNA sequence corresponding to oriP of EBV by the wild-type protein, is not significantly degraded, e.g., by the ubiquitin/proteosome pathway and/or does not elicit a significant immune response associated with MHC class I presentation of antigen, and/or localizes to the nucleus when present in a cell or organism, as a result of the presence of a DNA binding and dimerization sequence, a repeat of Gly-Gly-Ala, Gly-Ala-Gly, Ala-Gly-Ala, Ala-Gly-Gly, Gly-Gly-Gly, or a combination thereof, and a nuclear localization sequence, respectively. "LR1" is a sequence in a lymphotrophic herpes virus which corresponds to residues 40 to 89 in EBNA-1, e.g., residues 40 to 80 in SEQ ID NO:1 (Met Ser Asp Glu Gly Pro Gly Thr Gly Pro Gly Asn Gly Leu Gly Glu Lys Gly Asp Thr Ser Gly Pro Glu Gly Ser Gly Gly Ser Gly Pro Gln Arg Arg Gly Gly Asp Asn His Gly Arg Gly Arg Gly Arg Gly Arg Gly Arg Gly Gly Gly Arg Pro Gly Ala Pro Gly Gly Ser Gly Ser Gly Pro Arg His Arg Asp Gly Val Arg Arg Pro Gln Lys Arg Pro Ser Cys Ile Gly Cys Lys Gly Thr His Gly Gly Thr Gly Ala Gly Ala Gly Ala Gly Gly Ala Gly Ala Gly Gly Ala Gly Ala Gly Gly Gly Ala Gly Ala Gly Gly Gly Ala Gly Gly Ala Gly Gly Ala Gly Gly Ala Gly Ala Gly Gly Gly Ala Gly Ala Gly Gly Gly Ala Gly Gly Ala Gly Gly Ala Gly Ala Gly Gly Gly Ala Gly Ala Gly Gly Gly Ala Gly Gly Ala Gly Ala Gly Gly Gly Ala Gly Gly Ala Gly Gly Ala Gly Ala Gly Gly Gly Ala Gly Ala Gly Gly Gly Ala Gly Gly Ala Gly Ala Gly Gly Gly Ala Gly Gly Ala Gly Gly Ala Gly Ala Gly Gly Gly Ala Gly Ala Gly Gly Ala Gly Gly Ala Gly Gly Ala Gly Ala Gly Ala Gly Gly Ala Gly Ala Gly Gly Gly Ala Gly Gly Ala Gly Gly Ala Gly Ala Gly Gly Ala Gly Ala Gly Gly Ala Gly Ala Gly Gly Ala Gly Ala Gly Gly Ala Gly Ala Gly Gly Ala Gly Gly Ala Gly Ala Gly Ala Gly Gly Ala Gly Ala Gly Gly Ala Gly Gly Ala Gly Ala Gly Ala Gly Gly Gly Ala Gly Gly Ala Gly Ala Gly Gly Gly Ala Gly Gly Ala Gly Ala Gly Ala Gly Gly Ala Gly Gly Ala Gly Ala Gly Gly Ala Gly Gly Ala Gly Ala Gly Gly Ala Gly Ala Gly Gly Ala Gly Gly Ala Gly Ala Gly Gly Ala Gly Gly Ala Gly Ala Gly Gly Ala Gly Ala Gly Gly Gly Gly Arg Gly Arg Gly Gly Ser Gly Gly Arg Gly Arg Gly Gly Ser Gly Gly Arg Gly Arg Gly Gly Ser Gly Gly Arg Arg Gly Arg Gly Arg Glu Arg Ala Arg Gly Gly Ser Arg Glu Arg Ala Arg Gly Arg Gly Arg Gly Arg Gly Glu Lys Arg Pro Arg Ser Pro Ser Ser Gln Ser Ser Ser Ser Gly Ser Pro Pro Arg Arg Pro Pro Pro Gly Arg Arg Pro Phe Phe His Pro Val Gly Glu Ala Asp Tyr Phe Glu Tyr His Gln Glu Gly Gly Pro Asp Gly Glu Pro Asp Val Pro Pro Gly Ala Ile Glu Gln Gly Pro Ala Asp Asp Pro Gly Glu Gly Pro Ser Thr Gly Pro Arg Gly Gln Gly Asp Gly Gly Arg Arg Lys Lys Gly Gly Trp Phe Gly Lys His Arg Gly Gln Gly Gly Ser Asn Pro Lys Phe Glu Asn Ile Ala Glu Gly Leu Arg Ala Leu Leu Ala Arg Ser His Val Glu Arg Thr Thr Asp Glu Gly Thr Trp Val Ala Gly Val Phe Val Tyr Gly Gly Ser Lys Thr Ser Leu Tyr Asn Leu Arg Arg Gly Thr Ala Leu Ala Ile Pro Gln Cys Arg Leu Thr Pro Leu Ser Arg Leu Pro Phe Gly Met Ala Pro Gly Pro Gly Pro Gln Pro Gly Pro Leu Arg Glu Ser Ile Val Cys Tyr Phe Met Val Phe Leu Gln Thr His Ile Phe Ala Glu Val Leu Lys Asp Ala Ile Lys Asp Leu Val Met Thr Lys Pro Ala Pro Thr Cys Asn Ile Arg Val Thr Val Cys Ser Phe Asp Asp Gly Val Asp Leu Pro Pro Trp Phe Pro Pro Met Val Glu Gly Ala Ala Ala Glu Gly Asp Asp Gly Asp Asp Gly Asp Glu Gly Gly Asp Gly Asp Glu Gly Glu Glu Gly Gln Glu), e.g., GRGRGRGRGRG GGRP-GAPGGS GSGPRHRDGV RRPQKRPSCI GCKGTHGGT (SEQ ID NO:5), at least a portion of which in wild-type EBNA-1 is a transcriptional activation domain for integrated templates. The "unique region" of LR1 corresponds to residues 60 to 89 of EBNA-1. In one embodiment, a derivative of the invention lacks the following sequence SGSG-PRHRDGVRRPQKRPSCI GCKGTHGGT (SEQ ID NO:6), or lacks a portion thereof. In one embodiment, the derivative has substantial identity, e.g., at least 80% or more, e.g., 85%, 90% or 95% and up to 100%, amino acid sequence identity, to a wild-type protein corresponding to EBNA-1, e.g., SEQ ID NO:1, for instance, substantial identity to residues from about residue 90 to the residue corresponding to the C-terminus of the wild-type protein, or any integer in between, and optionally also has substantial identity from residue 1 to about residue 20, and up to about residue 60, or any integer in between, of the corresponding wild-type protein. "About" as used herein with respect to a particular residue means within 5 residues of the specified residue, e.g., within 1, 2, 3, 4 or 5 residues of residue "X" corresponding to residue "X" in SEQ ID NO:1.

An "origin of replication" ("ori") is a DNA sequence, e.g., in a lymphotrophic herpes virus, that when present in a plasmid in a cell is capable of maintaining linked sequences in the plasmid, and/or a site at or near where DNA synthesis initiates. An ori for EBV includes FR sequences (20 imperfect copies of a 30 bp repeat), and preferably DS sequences, however, other sites in EBV bind EBNA-1, e.g., Site III and Rep* sequences, can substitute for DS as an origin of replication (Kirchmaier and Sudgen, 1998). Thus, a DNA sequence which binds a protein corresponding to EBNA-1 includes FR, DS, Site III, and Rep* sequences.

A "lymphotrophic" herpes virus is a herpes virus that replicates in a lymphoblast (e.g., a human B lymphoblast) and becomes a plasmid for a part of its natural life-cycle. After infecting a host, these viruses latently infect the host by maintaining the viral genome as a plasmid. Herpes simplex virus (HSV) is not a "lymphotrophic" herpes virus. Exemplary lymphotropic herpes viruses include, but are not limited to EBV, Kaposi's sarcoma herpes virus (KSHV); Herpes virus saimiri (HS) and Marek's disease virus (MDV).

A "vector" or "construct" (sometimes referred to as gene delivery or gene transfer "vehicle") refers to a macromolecule or complex of molecules comprising a polynucleotide to be delivered to a host cell, either in vitro or in vivo. The polynucleotide to be delivered may comprise a coding sequence of interest for gene therapy. Vectors include, for example, viral vectors (such as adenoviruses, adeno-associated viruses (AAV), lentiviruses, herpesvirus and retroviruses), liposomes and other lipid-containing complexes, and other macromolecular complexes capable of mediating delivery of a polynucleotide to a host cell. Vectors can also comprise other components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. Large varieties of such vectors are known in the art and are generally available. When a vector is maintained in a host cell, the vector can either be stably replicated by the cells during mitosis as an autonomous structure, incorporated within the genome of the host cell, or maintained in the host cell's nucleus or cytoplasm.

A "recombinant viral vector" refers to a viral vector comprising one or more heterologous genes or sequences. Since many viral vectors exhibit size constraints associated with packaging, the heterologous genes or sequences are typically introduced by replacing one or more portions of the viral genome. Such viruses may become replication-defective, requiring the deleted function(s) to be provided in trans during viral replication and encapsidation (by using, e.g., a helper virus or a packaging cell line carrying genes necessary for replication and/or encapsidation). Modified viral vectors in which a polynucleotide to be delivered is carried on the outside of the viral particle have also been described.

"Gene delivery," "gene transfer," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art.

By "transgene" is meant any piece of a nucleic acid molecule (for example, DNA) which is inserted by artifice into a cell either transiently or permanently, and becomes part of the organism if integrated into the genome or maintained extrachromosomally. Such a transgene includes at least a portion of an open reading frame of a gene which is partly or entirely heterologous (i.e., foreign) to the transgenic organism, or may represent an open reading frame or a portion thereof of a gene homologous to an endogenous gene of the organism, which portion optionally encodes a polypeptide with substantially the same activity as the corresponding full length polypeptide, e.g., wild-type polypeptide, or at least one activity of the corresponding full length polypeptide.

By "transgenic cell" is meant a cell containing a transgene. For example, a stem cell transformed with a vector containing an expression cassette can be used to produce a population of cells having altered phenotypic characteristics. A "recombinant cell" is one which has been genetically modified, e.g., by insertion, deletion or replacement of sequences in a nonrecombinant cell by genetic engineering.

The term "wild-type" or "native" refers to a gene or gene product that has the characteristics of that gene or gene product when isolated from a naturally occurring source. A wild-type gene is that which is most frequently observed in a population and is thus arbitrarily designated the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "transduction" denotes the delivery of a polynucleotide to a recipient cell either in vivo or in vitro, via a viral vector and preferably via a replication-defective viral vector.

The term "heterologous" as it relates to nucleic acid sequences such as gene sequences and control sequences, denotes sequences that are not normally joined together, and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature, i.e., a heterologous promoter. Another example of a heterologous coding sequence is a construct where the coding sequence itself is not found in nature (e.g., synthetic sequences having codons different from the native gene). Similarly, a cell transformed with a construct which is not normally present in the cell would be considered heterologous for purposes of this invention.

By "DNA" is meant a polymeric form of deoxyribonucleotides (adenine, guanine, thymine, or cytosine) in double-stranded or single-stranded form found, inter alia, in linear DNA molecules (e.g., restriction fragments), viruses, plasmids, and chromosomes. In discussing the structure of particular DNA molecules, sequences may be described herein according to the normal convention of giving only the sequence in the 5' to 3' direction along the nontranscribed strand of DNA (i.e., the strand having the sequence complementary to the mRNA). The term captures molecules that include the four bases adenine, guanine, thymine, or cytosine, as well as molecules that include base analogues which are known in the art.

As used herein, the terms "complementary" or "complementarity" are used in reference to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotide or polynucleotide is referred to as the "5'end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

A "gene," "polynucleotide," "coding region," "sequence," "segment," "fragment," or "transgene" which "encodes" a particular protein, is a nucleic acid molecule which is transcribed and optionally also translated into a gene product, e.g., a polypeptide, in vitro or in vivo when placed under the control of appropriate regulatory sequences. The coding region may be present in either a cDNA, genomic DNA, or RNA form. When present in a DNA form, the nucleic acid molecule may be single-stranded (i.e., the sense strand) or double-stranded. The boundaries of a coding region are determined by a start codon at the 5' (amino) terminus and a translation stop codon at the 3' (carboxy) terminus. A gene can include, but is not limited to, cDNA from prokaryotic or eukaryotic mRNA, genomic DNA sequences from prokaryotic or eukaryotic DNA, and synthetic DNA sequences. A transcription termination sequence will usually be located 3' to the gene sequence.

The term "control elements" refers collectively to promoter regions, polyadenylation signals, transcription termination sequences, upstream regulatory domains, origins of replication, internal ribosome entry sites ("IRES"), enhancers, splice junctions, and the like, which collectively provide for the replication, transcription, post-transcriptional processing and translation of a coding sequence in a recipient cell. Not all of these control elements need always be present so long as the selected coding sequence is capable of being replicated, transcribed and translated in an appropriate host cell.

The term "promoter" is used herein in its ordinary sense to refer to a nucleotide region comprising a DNA regulatory sequence, wherein the regulatory sequence is derived from a gene which is capable of binding RNA polymerase and initiating transcription of a downstream (3' direction) coding sequence.

By "enhancer" is meant a nucleic acid sequence that, when positioned proximate to a promoter, confers increased transcription activity relative to the transcription activity resulting from the promoter in the absence of the enhancer domain.

By "operably linked" with reference to nucleic acid molecules is meant that two or more nucleic acid molecules (e.g., a nucleic acid molecule to be transcribed, a promoter, and an enhancer element) are connected in such a way as to permit transcription of the nucleic acid molecule. "Operably linked" with reference to peptide and/or polypeptide molecules is meant that two or more peptide and/or polypeptide molecules are connected in such a way as to yield a single polypeptide chain, i.e., a fusion polypeptide, having at least one property of each peptide and/or polypeptide component of the fusion. The fusion polypeptide is preferably chimeric, i.e., composed of heterologous molecules.

"Homology" refers to the percent of identity between two polynucleotides or two polypeptides. The correspondence between one sequence and to another can be determined by techniques known in the art. For example, homology can be determined by a direct comparison of the sequence information between two polypeptide molecules by aligning the sequence information and using readily available computer programs. Alternatively, homology can be determined by hybridization of polynucleotides under conditions which form stable duplexes between homologous regions, followed by digestion with single strand-specific nuclease(s), and size determination of the digested fragments. Two DNA, or two polypeptide, sequences are "substantially homologous" to each other when at least about 80%, preferably at least about 90%, and most preferably at least about 95% of the nucleotides, or amino acids, respectively match over a defined length of the molecules, as determined using the methods above.

By "mammal" is meant any member of the class Mammalia including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats, rabbits and guinea pigs, and the like.

By "derived from" is meant that a nucleic acid molecule was either made or designed from a parent nucleic acid molecule, the derivative retaining substantially the same functional features of the parent nucleic acid molecule, e.g., encoding a gene product with substantially the same activity as the gene product encoded by the parent nucleic acid molecule from which it was made or designed.

By "expression construct" or "expression cassette" is meant a nucleic acid molecule that is capable of directing transcription. An expression construct includes, at the least, a promoter. Additional elements, such as an enhancer, and/or a transcription termination signal, may also be included.

The term "exogenous," when used in relation to a protein, gene, nucleic acid, or polynucleotide in a cell or organism refers to a protein, gene, nucleic acid, or polynucleotide which has been introduced into the cell or organism by artificial or natural means, or in relation a cell refers to a cell which was isolated and subsequently introduced to other cells or to an organism by artificial or natural means. An exogenous nucleic acid may be from a different organism or cell, or it may be one or more additional copies of a nucleic acid which occurs naturally within the organism or cell. An exogenous cell may be from a different organism, or it may be from the same organism. By way of a non-limiting example, an exogenous nucleic acid is in a chromosomal location different from that of natural cells, or is otherwise flanked by a different nucleic acid sequence than that found in nature.

The term "isolated" when used in relation to a nucleic acid, peptide, polypeptide or virus refers to a nucleic acid sequence, peptide, polypeptide or virus that is identified and separated from at least one contaminant nucleic acid, polypeptide or other biological component with which it is ordinarily associated in its natural source. Isolated nucleic acid, peptide, polypeptide or virus is present in a form or setting that is different from that in which it is found in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. The isolated nucleic acid molecule may be present in single-stranded or double-stranded form. When an isolated nucleic acid molecule is to be utilized to express a protein, the molecule will contain at a minimum the sense or coding strand (i.e., the molecule may single-stranded), but may contain both the sense and anti-sense strands (i.e., the molecule may be double-stranded).

The term "recombinant DNA molecule" as used herein refers to a DNA molecule that is comprised of segments of DNA joined together by means of molecular biological techniques.

The term "recombinant protein" or "recombinant polypeptide" as used herein refers to a protein molecule that is expressed from a recombinant DNA molecule.

The terms "peptide", "polypeptide" and protein" are used interchangeably herein unless otherwise distinguished.

The term "sequence homology" means the proportion of base matches between two nucleic acid sequences or the proportion amino acid matches between two amino acid sequences. When sequence homology is expressed as a percentage, e.g., 50%, the percentage denotes the proportion of matches over the length of a selected sequence that is compared to some other sequence. Gaps (in either of the two sequences) are permitted to maximize matching; gap lengths of 15 bases or less are usually used, 6 bases or less are preferred with 2 bases or less more preferred. When using oligonucleotides as probes or treatments, the sequence homology between the target nucleic acid and the oligonucleotide sequence is generally not less than 17 target base matches out of 20 possible oligonucleotide base pair matches (85%); preferably not less than 9 matches out of 10 possible base pair matches (90%), and more preferably not less than 19 matches out of 20 possible base pair matches (95%).

The term "selectively hybridize" means to detectably and specifically bind. Polynucleotides, oligonucleotides and fragments of the invention selectively hybridize to nucleic acid strands under hybridization and wash conditions that minimize appreciable amounts of detectable binding to nonspecific nucleic acids. High stringency conditions can be used to achieve selective hybridization conditions as known in the art and discussed herein. Generally, the nucleic acid sequence homology between the polynucleotides, oligonucleotides, and fragments of the invention and a nucleic acid sequence of interest is at least 65%, and more typically with preferably increasing homologies of at least about 70%, about 90%, about 95%, about 98%, and 100%.

Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. The two sequences or parts thereof are more preferably homologous if their amino acids are greater than or equal to 50% identical when optimally aligned using the ALIGN program.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing, or may comprise a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity.

A "comparison window", as used herein, refers to a conceptual segment of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by homology alignment algorithms, including computerized implementations of algorithms, or by inspection, and the best alignment (i.e., resulting in the highest percentage of homology over the comparison window) generated by the various methods is selected.

The term "sequence identity" means that two polynucleotide sequences are identical (i.e., on a nucleotide-by-nucleotide basis) over the window of comparison. The term "percentage of sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denote a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 20-50 nucleotides, wherein the percentage of sequence identity is calculated by comparing the reference sequence to the polynucleotide sequence which may include deletions or additions which total 20 percent or less of the reference sequence over the window of comparison.

As applied to polypeptides, the term "substantial identity" means that two peptide sequences, when optimally aligned, such as by the programs GAP or BESTFIT using default gap weights, share at least about 80 percent sequence identity, preferably at least about 90 percent sequence identity, more preferably at least about 95 percent sequence identity, and most preferably at least about 99 percent sequence identity.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, about 90%, about 95%, and about 99%. Most preferably, the object species is purified to essential homogeneity (contaminant species cannot be detected in the composition by conventional detection methods) wherein the composition consists essentially of a single macromolecular species.

The term "prophylactically effective amount" is meant to refer to the amount necessary to, in the case of infectious agents, prevent an individual from developing an infection, and in the case of diseases, prevent an individual from developing a disease.

The term "therapeutically effective amount" is meant to refer to the amount necessary to, in the case of infectious agents, reduce the level of infection in an infected individual in order to reduce symptoms or eliminate the infection, and in the case of diseases, to reduce symptoms or cure the individual.

"Inducing an immune response against an immunogen" is meant to refer to induction of an immune response in a naïve individual and induction of an immune response in an individual previously exposed to an immunogen wherein the immune response against the immunogen is enhanced.

Preparation of Vectors

To prepare vectors which may include expression cassettes with one or more desirable open reading frames for transformation herein, the vector may be circular or linear, double-stranded or single-stranded. A DNA sequence which encodes an RNA sequence that is substantially complementary to a mRNA sequence encoding a gene product of interest is typically a "sense" DNA sequence cloned into a cassette in the opposite orientation (i.e., 3' to 5' rather than 5' to 3'). Generally, the vector is in the form of chimeric DNA, such as plasmid DNA, that can also contain coding regions flanked by control sequences which promote the expression of the DNA in a cell. As used herein, "chimeric" means that a vector comprises DNA from at least two different species, or comprises DNA from the same species, which is linked or associated in a manner which does not occur in the "native" or wild-type of the species.

Aside from DNA sequences that serve as transcription units, or portions thereof, a portion of the DNA may be untranscribed, serving a regulatory or a structural function. For example, the DNA may itself comprise a promoter that is active in eukaryotic cells, e.g., mammalian cells, or in certain cell types, or may utilize a promoter already present in the genome that is the transformation target of the lymphotropic virus. Such promoters include the CMV promoter, as well as the SV40 late promoter and retroviral LTRs (long terminal repeat elements), e.g., the MMTV, RSV, MLV or HIV LTR, although many other promoter elements well known to the art may be employed in the practice of the invention.

Other elements functional in the host cells, such as introns, enhancers, polyadenylation sequences and the like, may also be a part of the recombinant vector. Such elements may or may not be necessary for the function of the DNA, but may provide improved expression of the DNA by affecting transcription, stability of the mRNA, or the like. Such elements may be included in the DNA as desired to obtain the optimal performance of the transforming DNA in the cell.

The recombinant vector to be introduced into the cells may contain either a selectable marker gene, such as those encoding puromycin resistance, hygromycin B resistance, or G418 sulfate resistance, or a reporter gene or both to facilitate identification and selection of transformed cells from the population of cells sought to be transformed. Alternatively, the selectable marker may be carried on a separate piece of DNA and used in a co-transformation procedure. Both selectable markers and reporter genes may be flanked with appropriate regulatory sequences to enable expression in the host cells. Useful selectable markers are well known in the art and include, for example, antibiotic and herbicide-resistance genes, such as neo, hpt, dhfr, bar, aroA, puro, hyg, dapa and the like. See also, the genes listed on Table 1 of Lundquist et al. (U.S. Pat. No. 5,848,956).

Reporter genes are used for identifying potentially transformed cells and for evaluating the functionality of regulatory sequences. Reporter genes which encode for easily assayable proteins are well known in the art. In general, a reporter gene is a gene which is not present in or expressed by the recipient organism or tissue and which encodes a protein whose expression is manifested by some easily detectable property, e.g., enzymatic activity. Exemplary reporter genes include the chloramphenicol acetyl transferase gene (cat) from Tn9 of *E. coli*, the beta-glucuronidase gene (gus) of the uidA locus of *E. coli*, the green, red, or blue fluorescent protein gene, and the luciferase gene. Expression of the reporter gene is assayed at a suitable time after the DNA has been introduced into the recipient cells.

The general methods for constructing recombinant DNA which can transform target cells are well known to those skilled in the art, and the same compositions and methods of construction may be utilized to produce the DNA useful herein.

The recombinant vector can be readily introduced into the host cells, e.g., mammalian, bacterial, yeast or insect cells, or prokaryotic cells, by any procedure useful for the introduction into a particular cell, e.g., physical or biological methods, to yield a transformed (transgenic) cell having the recombinant vector so that the DNA sequence of interest is maintained and expressed by the host cell. In one embodiment, the recombinant vector is maintained extrachromosomally, e.g., it is a circular plasmid. Physical methods to introduce a recombinant vector into a host cell include calcium-mediated methods, lipofection, particle bombardment, (micro)injection, electroporation, and the like. Biological methods to introduce DNA of interest into a host cell include the use of recombinant DNA or RNA viruses, e.g., poxviruses, herpes virus, adenoviruses, adeno-associated viruses, lentiviruses and retroviruses.

"Transfected," "transformed" or "transgenic" is used herein to include any host cell or cell line, which has been altered or augmented by the presence of at least one recombinant DNA sequence. The host cells of the present invention are typically produced by transfection with a DNA sequence in a plasmid expression vector, as an isolated linear DNA sequence, or infection with a recombinant viral vector.

To confirm the presence of the recombinant DNA sequence in the host cell, a variety of assays may be performed. Such assays include, for example, molecular biological assays well known to those of skill in the art, such as Southern and Northern blotting, RT-PCR and PCR; biochemical assays, such as detecting the presence or absence of a particular gene product, e.g., by immunological means (ELISAs and Western blots) or by other molecular assays.

To detect and quantitate RNA produced from introduced recombinant DNA segments, RT-PCR may be employed. In this application of PCR, it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique demonstrates the presence of an RNA species and gives information about the integrity of that RNA. The presence or absence of an RNA species can also be determined using dot or slot blot Northern hybridizations. These techniques are modifications of Northern blotting and only demonstrate the presence or absence of an RNA species.

While Southern blotting and PCR may be used to detect the recombinant DNA segment in question, they do not provide information as to whether the recombinant DNA segment is being expressed. Expression may be evaluated by specifically identifying the peptide products of the introduced DNA sequences or evaluating the phenotypic changes brought about by the expression of the introduced DNA segment in the host cell.

In one embodiment of the invention, the vector also encodes EBNA-1 or a derivative thereof. In another embodiment, EBNA-1 or a derivative thereof is provided in trans, e.g., as a recombinant protein expressed from another vector, such as one stably integrated into a host cell genome. A derivative of the invention is a polypeptide which, relative to a corresponding wild-type polypeptide, has a modified amino acid sequence. The modifications include the deletion, insertion or substitution of at least one amino acid residue in a region corresponding to the unique region of LR1 in EBNA-1, and may include a deletion, insertion and/or substitution of one or more amino acid residues in regions corresponding to other residues of EBNA-1, e.g., about residue 1 to about residue 40, residues about 90 to about 328 ("Gly-Gly-Ala" repeat region), residues about 329 to about 377 (LR2), residues about 379 to about 386 (NLS), residues about 451 to about 608 (DNA binding and dimerization), or residues about 609 to about 641, so long as the resulting derivative has the desired properties, e.g., dimerizes and binds DNA containing an ori corresponding to oriP, localizes to the nucleus, is not cytotoxic, and activates transcription from an extrachromosomal template but does not substantially active transcription from an integrated template. Substitutions include substitutions which utilize the D rather than L form, as well as other well known amino acid analogs, e.g., unnatural amino acids such as α,α-disubstituted amino acids, N-alkyl amino acids, lactic acid, and the like. These analogs include phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoyl-phenylalanine, phenylglycine, propargylglycine, sarcosine, ϵ-N,N,N-trimethyllysine, ϵ-N-acetyllysine, N-acetylserine, N-formylmethionine, 3-methylhistidine, 5-hydroxylysine, ω-N-methylarginine, and other similar amino acids and imino acids and tert-butylglycine.

Conservative amino acid substitutions are preferred—that is, for example, aspartic-glutamic as polar acidic amino acids; lysine/arginine/histidine as polar basic amino acids; leucine/isoleucine/methionine/valine/alanine/glycine/proline as nonpolar or hydrophobic amino acids; serine/threonine as polar or uncharged hydrophilic amino acids. Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting polypeptide. Whether an amino acid change results in a functional polypeptide can readily be determined by assaying the specific activity of the polypeptide.

Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic; trp, tyr, phe.

The invention also envisions polypeptides with non-conservative substitutions. Non-conservative substitutions entail exchanging a member of one of the classes described above for another.

Compositions, Formulations and Uses of the Vectors

The vectors of the invention may be employed in vitro, ex vivo, i.e., cells to be introduced to an eukaryotic organism, e.g., a mammal, or in vivo, e.g., as a gene transfer vector useful to transfer therapeutic or prophylactic gene products. The amount of vector(s) administered will vary depending on various factors including, but not limited to, the vector(s) chosen, the condition or disease, and whether prevention or treatment is to be achieved. Administration of the vectors in accordance with the present invention may be continuous or intermittent. Both local and systemic administration is contemplated.

The use of plasmid- or liposome-based vectors, e.g., oriP-based vectors, and/or vectors encoding the Gly-Gly-Ala repeat of EBNA-1 permit large fragments of DNA to be introduced to a cell and maintained extrachromosomally, replicated once per cell cycle, partitioned to daughter cells efficiently, and elicit substantially no immune response. In particular, EBNA-1, the only viral protein required for the replication of the oriP-based expression vector, does not elicit a cellular immune response because it has developed an efficient mechanism to bypass the processing required for presentation of its antigens on MHC class 1 molecules (Levitskaya et al., 1997). Further, EBNA-1 can act in trans to enhance expression of the cloned gene, inducing expression of a cloned gene up to 100-fold in some cell lines (Langle-Rouault et al., 1998; Evans et al., 1997). Finally, the manufacture of such oriP-based expression vectors is inexpensive.

One application of oriP-based expression vectors is the delivery of a wild-type gene to cells in which both alleles for the gene are defective. An oriP plasmid can be constructed which supports expression of EBNA-1, the gene of interest, and a selectable marker. Lei et al. (1996) used an oriP-based vector to deliver the cystic fibrosis transmembrane conductance regulator (CFTR) gene to transformed human airway epithelial cells defective in cAMP-dependent chloride transport. Transfection of this vector into the indicated cells led to the restoration of cAMP-dependent chloride transport. The rate of loss for oriP plasmids is a function of the number of cell cycles through which a host cell passes without selection (Kirchmaier et al., 1995). Generally, the plasmids are lost at about 3%/cell/generation in the absence of selection. Because most cells in adults proliferate slowly or not at all, oriP/EBNA-1 vectors are likely to be maintained in them for long times. Therefore, airway epithelial cells in adults are likely ideal targets for this type of therapy. If oriP plasmids are targeted to rapidly dividing cells, it may be necessary to re-administered them periodically or provide the cells which carry the oriP plasmids with a selective advantage.

OriP-based expression vectors can also be used to target genes to tumour cells. Hirai et al. (1997) developed a system to target therapeutic agents to EBV-positive cells. They designed an oriP plasmid which contained the HSV thymidine kinase gene driven by its native promoter. EBNA-1-positive and -negative cells were transfected with this plasmid via envelope proteins from inactivated Haemagglutinating Virus of Japan (HVJ, or Sendai virus), treated with 30 mM gancyclovir at 3 days post-transfection and monitored for viability at different time points. After 3 days of treatment with gancyclovir, less than 10% of the EBNA-1-positive cells were viable, whereas toxicity was not detected in EBNA-1-negative cell lines. This approach, in which HVJ-liposomes are used to target oriP plasmids to EBNA-1-positive cells, may prove valuable for treating EBV-associated malignancies. HVJ-liposomes have been successfully used to deliver marker genes into bone marrow cells and human primary fibroblasts and so are a delivery system for oriP-based expression vectors.

To introduce a vector into target cells other than B lymphocytes, inoculation of naked DNA, e.g., using electroporation, iontophoresis or particle-mediated delivery, complexing the DNA with polycations such as cationic lipids or cationic polymers (Dubensky et al., 1984; Felgner et al., 1989; Perales et al., 1994; Wolff et al., 1990) or polyanions (Kaneda, 2001), e.g., liposome-mediated gene transfer, may be employed. These methods may be employed to deliver the gene repeatedly if rapidly proliferating cells are the requisite targets for gene transfer.

OriP-based vectors not only are potentially effective tools in gene therapy, but may also be used to advantage in cell culture. An oriP vector into which a gene of interest has been cloned can be maintained extrachromosomally in many mammalian cells which express EBNA-1 (Yates et al., 1984). The EBNA-1 moiety of this replicon can be expressed either as a gene integrated into the host cell or as a gene incorporated into the vector. The former approach has the advantage of a 10- to 100-fold increase in the number of transfected cells that support extrachromosomal replication of the oriP vector (Peterson et al., 1991). The latter approach provides versatility to the use of a single vector in many cell types.

OriP/EBNA-1 replicons have been used to study gene expression with at least three different goals. First, the expressed genes have been dissected genetically to elucidate their functions via the phenotypes they induce. The efficient expression of genes from oriP vectors facilitates these experiments (Langle-Rouault et al., 1998; Evens et al., 1997). Second, the transcriptional regulation of genes expressed from oriP vectors has been analysed genetically. These analyses allow mutagenesis of cis-acting elements within a promoter and measurements of transcription from the promoter in a population of cells which have been selected to maintain the plasmid replicon. Third, the plasmid nature of oriP vectors allows their ready isolation from transfected cells and has permitted the development of selections in mammalian cells for expressed genes which compensate for defects in the recipient cells.

A major application of genes expressed from oriP vectors has been to analyse genetically cis- and trans-acting elements of EBV itself. Genetic studies of EBNA-1, EBNA-2, LMP-1, oriP and oriLyt have all been conducted with oriP expression vectors. This use of oriP vectors has been extended to the study of cellular genes too. For example, the L1 retrotransposon has been introduced into an oriP vector and its rate of transposition to the host cell genome measured (Moran et al., 1996). Mutations introduced into an open reading frame of the retrotransposon affected the rate of retrotransposition and confirmed the role of this open reading frame in retrotransposition.

The chromatin structure of genes inserted into oriP vectors, as exemplified by the HIV provirus, appears similar or identical to that of genes integrated into the cellular genome (Stanfield-Oakley et al., 1996). These observations make oriP/EBNA-1 vectors desirable vehicles for the analysis of the regulation of gene expression. Stretches of 50 kbp of DNA from the human c-myc locus have been cloned into a F-factor plasmid which contains oriP, propagated in $E.\ coli$, purified, and then introduced into EBV-positive cells which provide EBNA-1 in trans. Cis-acting enhancers from the immunoglobulin locus were shown to activate transcription of c-myc even when the enhancers were located 30 kbp away (Mautner et al., 1996).

A third application of oriP/EBNA-1 plasmids is to select for expressed genes in a library of oriP vectors which carry a cDNA or genomic DNA that complement a defect in a recipient cell or otherwise provide the recipient cell a selective advantage. This application has been used effectively to search for wild-type genes which when mutant render cells susceptible to efficient killing with ultraviolet light. The wild-type cDNA of a gene mutated in cells of a patient with xeroderma pigmentosum group C(XP-C) was recovered on an oriP vector after its selection in XP-C cells exposed to UV-light in cell culture (Legerski et al., 1992). An analogous selection has been used successfully to isolate a wild-type cDNA of the CSA gene mutated in hereditary Cockayne Syndrome. This application will also be rendered more facile by the use of YAC and BAC libraries in which the vectors have incorporated oriP (Simpson et al., 1996; Henning et al., 1995).

For gene therapy, the vectors of the invention may be introduced to any mammal, e.g., a mammal having symptoms of a genetically-based disorder, an acquired disorder or an infectious disease which is amenable to gene-based therapy, including but not limited to bovine, ovine, equine, caprine, canine, feline, and porcine, as well as primates, particularly humans.

In one embodiment, gene transfer in vivo is obtained by introducing an expression vector into the mammalian host, either as naked DNA, recombinant virus or DNA complexed to charged carriers, e.g., cationic lipid carriers, or by introducing autologous or allogeneic donor cells, such as non-adherent autologous or allogeneic stem cells, including pluripotent cells such as pluripotent hematopoietic stem cells, that are genetically altered with the vector of the invention to the mammalian host. The vectors may provide for integration into the host or donor cell genome for stable maintenance of the transgene encoding the derivative of the invention or for episomal expression of a prophylactic or therapeutic transgene. The introduction into the mammalian host may be by any of several routes, including intravenous or intraperitoneal injection, intratracheally, intrathecally, parenterally, intraarticularly, intranasally, intramuscularly, topical, transdermal, application to any mucous membrane surface, corneal instillation, and the like. For instance, an expression vector or genetically modified donor cell may be introduced into a circulating bodily fluid or into a body orifice or cavity, such as lung, colon, vagina, and the like, or intrathecal administration, which may result in wide dissemination of the vector following such routes of administration. In one embodiment, aerosol administration is employed to introduce a vector into a body orifice or cavity. Any physiologically acceptable medium may be employed for administering the DNA, recombinant virus or lipid carriers, such as deionized water, saline, phosphate-buffered saline, 5% dextrose in water, and the like, depending upon the route of administration. Other components may be included in the formulation such as buffers, stabilizers, biocides, and the like.

The amount of naked DNA, recombinant virus or complexes, or genetically modified donor cells, used is an amount sufficient to provide for adequate dissemination to a variety of tissues after entry of the DNA, recombinant virus or complexes, or genetically modified donor cells, into the bloodstream and to provide for a therapeutic or prophylactic level of expression in at least some transfected or infected tissues. A therapeutic or prophylactic level of expression is a sufficient amount of expression to prevent, treat or palliate a disease or infection of the mammal.

The formulations and compositions described herein may also contain other ingredients such as antimicrobial agents, or preservatives. Furthermore, the active ingredients may also be used in combination with other therapeutic agents Kits of the invention will generally include the DNA either as naked DNA or complexed to lipid carriers, and/or an isolated derivative of the invention. Additionally, lipid carriers may be provided in a separate container for complexing with the provided DNA. The DNA either for direct administration or for complexing with lipid carriers, or the lipid carrier/DNA complexes, and/or an isolated derivative of the invention may be present as concentrates which may be further diluted prior to use or they may be provided at the concentration of use, where the vials may include one or more dosages. Conveniently, single dosages may be provided in sterile vials so that the physician or veterinarian may employ the vials directly, where the vials will have the desired amount and concentration of agents. Thus, a vial may contain the DNA vector, the DNA vector/lipid carrier and/or donor cells with the vector of the invention in appropriate proportional amounts. When the vials contain the formulation for direct use, usually there will be no need for other reagents for use with the method.

For parenteral administration, sterile liquid pharmaceutical compositions, solutions or suspensions can be utilized by, for example, intraperitoneal injection, subcutaneous injection, intravenously, or topically. The vectors can be also be administered intravascularly or via an implantable device, e.g., a needle, catheter, shunt, or stent.

In addition, the vectors can be formulated for inhalation. The liquid carrier for pressurized compositions can be halogenated hydrocarbon or other pharmaceutically acceptable propellent. Such pressurized compositions are typically lipid encapsulated or associated for delivery via inhalation. For administration by intranasal or intrabronchial inhalation or insufflation, the vectors may be formulated into an aqueous or partially aqueous solution, which can then be utilized in the form of an aerosol, for example, for treatment of conditions affecting the respiratory tract, such as cystic fibrosis.

For viral delivery, vector particles which have been purified or concentrated may be preserved by first adding a sufficient amount of a formulation buffer to the media containing the particles, in order to form an aqueous suspension. The formulation buffer may be an aqueous solution that contains a saccharide, a high molecular weight structural additive, and a buffering component in water. As utilized within the context of the resent invention, a "buffering compound" or "buffering component" should be understood to refer to a substance that functions to maintain the aqueous suspension at a desired pH. The aqueous solution may also contain one or more amino acids.

The particles can also be preserved in a purified form. More specifically, prior to the addition of the formulation buffer, the crude particles may be clarified by passing through a filter, and then concentrated, such as by a cross flow concentrating system.

The crude particle preparation can also be purified by ion exchange column chromatography. In general, the crude particle preparation is clarified by passing it through a filter, and the filtrate loaded onto a column containing a highly sulfonated cellulose matrix. The particles are eluted from the column in purified form by using a high salt buffer. The high salt buffer is then exchanged for a more desirable buffer by passing the eluate over a molecular exclusion column. A sufficient amount of formulation buffer is then added, as discussed above, to the purified vector particle and the aqueous suspension is either dried immediately or stored, preferably at $-70°$ C. The aqueous suspension in crude or purified form can be dried by lyophilization or evaporation at ambient temperature. In the evaporative method, water is removed from the aqueous suspension at ambient temperature by evaporation. In one embodiment, water is removed through spray drying.

The aqueous solutions used for formulation may be composed of a saccharide, high molecular weight structural additive, a buffering component, and water. The solution may also include one or more amino acids. The combination of these components act to preserve the activity of the particles upon freezing and lyophilization, or drying through evaporation.

The lyophilized or dehydrated viruses may be reconstituted using a variety of substances, but are preferably reconstituted using water. Particles of the present invention may be administered to a wide variety of locations including, for example, into sites such as the cerebral spinal fluid, bone marrow, joints, arterial endothelial cells, rectum, buccal/sublingual, vagina, the lymph system, to an organ selected from the group consisting of lung, liver, spleen, skin, blood and brain, or to a site selected from the group consisting of tumors and interstitial spaces. Within other embodiments, the vector particle may be administered intraocularly, intranasally, sublingually, orally, topically, intravesically, intrathecally, topically, intravenously, intraperitoneally, intracranially, intramuscularly, or subcutaneously.

Exemplary Genes Useful in the Vectors of the Invention

A gene delivery vector may be designed to express any open reading frame, including but not limited to a therapeutic protein capable of preventing, inhibiting, stabilizing or reversing an inherited or noninherited genetic defect in metabolism, immune regulation, hormonal regulation, enzymatic or membrane associated structural function, or a prophylactic protein. Diseases which are amenable to treatment by a gene delivery vector of the invention include but are not limited to cystic fibrosis, Parkinson's disease, thalassemia, phenylketonuria, Lesch-Nyhan syndrome, severe combined immunodeficiency (SCID), Duchenne's Muscular Dystrophy, inherited emphysema, hypercholesterolemia, adenosine deaminase deficiency, β-globin disorders, α1antitrypsin (AAT) deficiency, hemophilia A, hemophilia B, Gaucher's disease, storage disease mucopolysaccharidosis type VII, hereditary lactose intolerance, diabetes, and leukemia, and the therapeutic gene may encode factor VIII, factor IX, factor V, adenosine deaminase, e.g., to treat leukemia arising from retroviral insertion (Schmidt et al., 2003), lactase, β-glucuronidase, antithrombin III, protein C, prothombin, or thrombomodulin, among others.

In addition the vectors can be used to produce anti-sense nucleic acids in cells. Antisense therapy involves the production of nucleic acids that bind to a target nucleic acid, typically an RNA molecule, located within cells. Antisense therapy generally employs oligonucleotides that are complementary to mRNA molecules ("sense strands") which encode a cellular product. Exemplary modes by which sequences can be targeted for therapeutic applications include: blocking the interaction of a protein with an RNA sequence (e.g., the interaction of RNA virus regulatory proteins with their RNA genomes); and targeting sequences causing inappropriate expression of cellular genes or cell proliferation (e.g., genes associated with cell cycle regulation; genetic disorders; and cancers (protooncogenes)). Exemplary potential target sequences are protooncogenes, oncogenes/tumor suppressor genes, transcription factors, and viral genes.

In addition, the vectors of the present invention can be used to deliver DNA sequences encoding catalytic RNA molecules into cells. For example, DNA sequences encoding a ribozyme of interest can be cloned into a vector of the present invention. Such a ribozyme may be a hammerhead ribozyme capable of cleaving a viral substrate, or an undesirable messenger RNA, such as that of an oncogene. The DNA-encoding ribozyme sequences can be expressed in tandem with tRNA sequences, with transcription directed from, for example, mammalian tRNA promoters.

Thus, exemplary gene products of interest for use with the vectors of the invention include but are not limited to, DNA sequences which code for an antisense or ribozyme sequence such as one to HIV-REV or a BCR-ABL sequence, code for proteins such as transdominant negative mutants which specifically prevent the integration of HIV genes into the host cell genomic DNA, replication of HIV sequences, translation of HIV proteins, processing of HIV mRNA, or virus packaging in human cells; code for wild-type conductance regulator (CFTR), wild-type p53, granulocyte macrophage colony stimulating factor (GM-CSF), as well as the LDL (low density lipoprotein) receptor, apo(a), phenylalanine hydroxylase, ornithine transcarboxylase (OTC), molecules which have superoxide dismutase activity, endothelial prostaglandin synthase, alpha-1 antitrypsin, erythropoietin, cytokines, e.g., IL-1, IL-2, IL-3, IL-4, IL-5, IL-6, IL-8, IL-9, IL-10, IL-11, IL-12, IL-13, IL-14, IL-15, and IL-18, the gamma chain of cytokine receptors (Kennedy and Sugden, 2003), alpha interferon, gamma interferons, G-CSF or tumor necrosis factors (TNFs), polypeptide or peptide hormones, blood clotting factors, phosphorylases, and kinases. Representative examples of antisense sequences include, but are not limited to, antisense thymidine kinase, antisense dihydrofolate reductase, antisense IL-1 receptor, antisense BER2, antisense ABL, antisense Myc, and antisense ras, as well as antisense sequences which block any of the enzymes in the nucleotide biosynthetic pathway, or antisense sequences for influenza virus, HIV, HSV, HPV, CMV, and HBV. Proteins of therapeutic interest for the treatment of coronary heart disease and congestive heart failure include fibroblast growth factors such as FGF-2 and beta adrenergic receptors.

Prophylactic compositions may comprise a vector encoding a gene product for which is desirable to produce an immune response, e.g., a response to pathogens including viruses, e.g., gB of HSV, bacteria, yeast and fungi, or tumor antigens.

Other open reading frames useful to deliver to a cell, e.g., an adult somatic cell so as to induce dedifferentiation of those cells, include, but are not limited to, those for Oct3, Oct4, Sox2, Klf4, c-myc, NANOG, LIN28, or combinations thereof.

The invention will be described by the following nonlimiting example.

EXAMPLE

Experimental Procedure

Plasmid Construction.

Figure 1B:
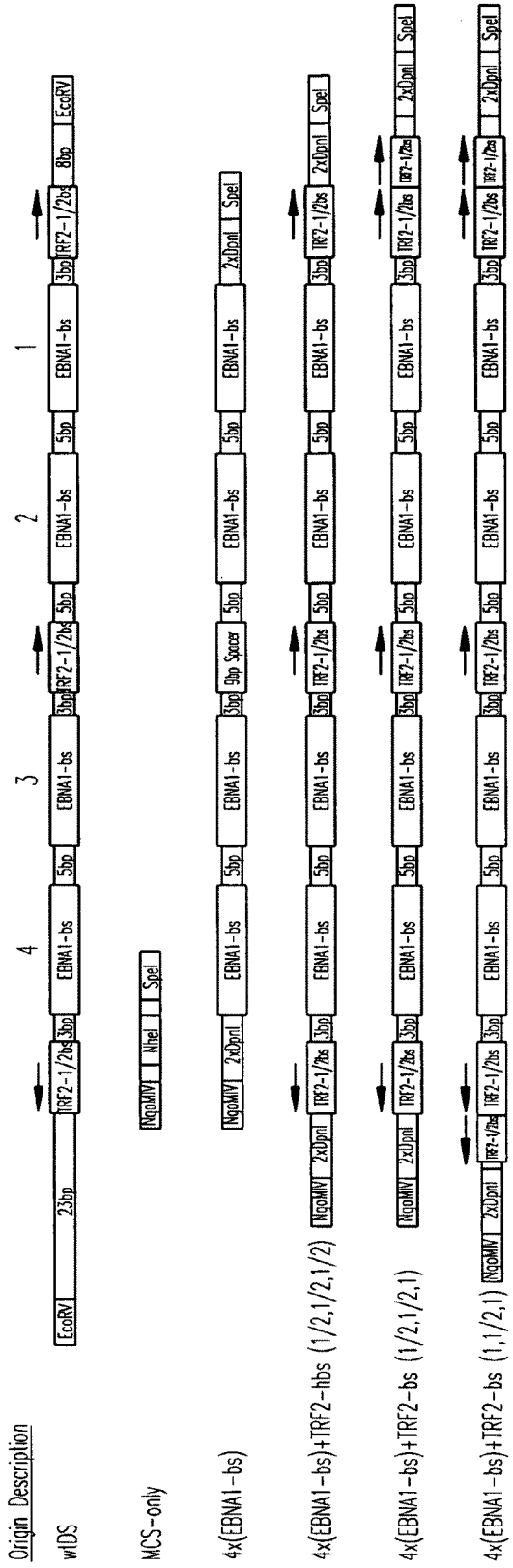
Figure 2:
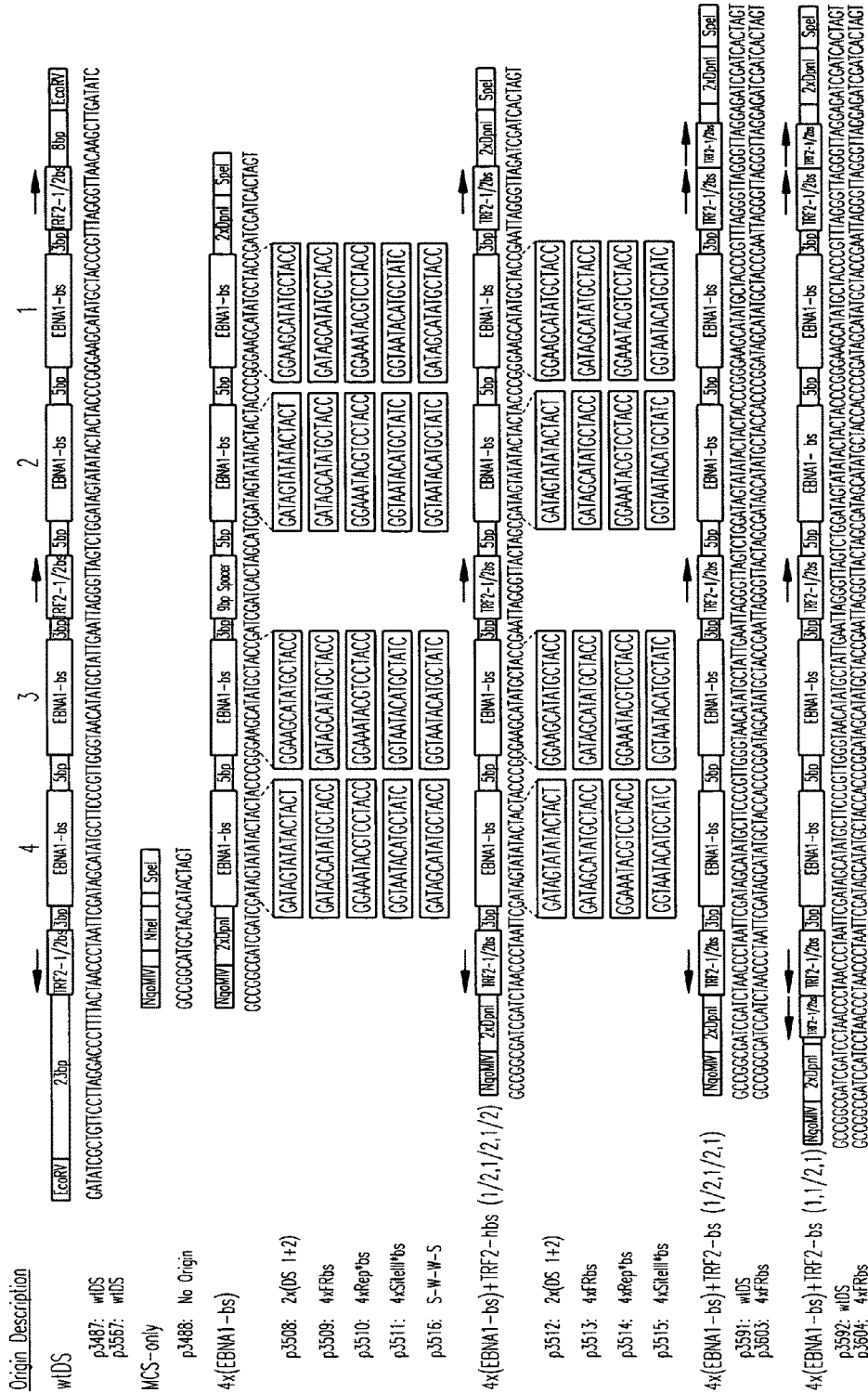
FIG. 2. Classes and sequences of each origin DNA synthesis tested. A graphical representation of each class of origin tested in depicted with the sequence of individual origins below it (SEQ ID NOs: 8-9 and 36-46). Within each class, only the sequences corresponding to the EBNA-1 binding sites differ.

All origins tested in this study are depicted graphically in FIG. 1. Complete representations of these origins, including their sequences, are given in FIG. 2. A positive-control oriP plasmid (p3487) was digested with EcoRV to remove the DS element and an artificial multiple cloning site (MCS) was inserted in its place to create a plasmid lacking origin activity (p3488, "MCS-only" plasmid). All origins were designed to position four naturally-occurring EBNA-1-binding sites of differing affinities (e.g., high-affinity: 4×FRbs, medium-affinity: 2×(DS1+2) and 4×SiteIIIbs, low-affinity 4×Rep*bs) in an arrangement identical to that found in the DS element. This arrangement was chosen to allow comparisons with the element EBV has evolved to use. The interaction between the TTAGGG-repeat Binding Factor 2 (TRF2) and EBNA-1 increases the apparent affinity of EBNA-1 for its binding site when a TRF2-half-binding site is positioned 3 bp away from it (Deng et al., 2002). Therefore derivatives of the engineered origins were constructed that would include three 9 bp TRF2-half-binding sites in the arrangement present in DS to determine if any further effect on DNA synthesis could be attributed to the interaction of TRF2 with ORC1 and/or EBNA-1. Lastly, because DS contains 2 EBNA-1-binding sites of higher affinity that are paired with 2 EBNA-1-binding sites of lower affinity, an origin from EBNA-1-binding sites derived from the high-affinity FR binding sites and the medium-affinity binding sites from Site III was prepared (Rawlins et al., 1985). This produced an origin with EBNA-1-binding sites in the same "strong-weak-weak-strong" (S-W-W-S) arrangement that is observed in DS, but of higher affinities than those found in wtDS.

All engineered origins of DNA synthesis were inserted between the NgoMIV and SpeI sites of the MCS (p3508-p3516, p3591, p3592, p3603, p3604). This strategy also preserved the sequences present in EBV between FR and DS. Moreover, the plasmids produced differ only in the sequence of the origin of DNA synthesis, thus avoiding the potential effects that any other sequence in cis might have on replicative function. In addition, wtDS was re-introduced into the MCS to control for effects caused by the residual bases introduced by the MCS (p3499). Finally, an additional positive-control plasmid (p3567) was created by inserting 1.2 kb of lambda phage DNA known not to support initiation of DNA synthesis into a unique EcoRI site present in the vector backbone of the parental oriP plasmid.

Cell Culture.

Raji, an EBV-positive cell line, and 293/EBNA-1, a human embryonic kidney cell line that stably expresses EBNA-1 and neomycin phosphotransferase (ATCC CRL 10852), have been previously described (Leight et al., 2001; Menezes et al., 1975; Pulvertaft, 1965). Raji cells were maintained in RPMI 1640 medium supplemented with 10% fetal bovine serum ("FBS", HyClone, Logan, Utah), 200 µl/mL penicillin, and 200 µg/mL streptomycin sulfate (GibcoBRL, Rockville, Md.) ("R10F") at 37° C. in a 5% $CO_2$ humidified atmosphere. 293/EBNA-1 cells were similarly maintained, but in Dulbecco's modified Eagle's medium (DMEM) with high glucose and supplemented with 10% fetal bovine serum, 200 U/mL of penicillin and 200 µg/mL of streptomycin sulfate, ("D10F") and 220 µg/mL G418 sulfate. Clones of Raji cells stably-transfected with the test plasmids were cultured under selection with 1 µg/mL puromycin.

Transfection.

Electroporation of $5 \times 10^6$ Raji cells was performed in 500 µL of R10F with a custom-built electroporator at 1100 V, 3 capacitor banks with 1540 microfarads of capacitance, R-adjust set at 6 o'clock, and a rise time set at 10 o'clock as described in Wang et al. (2006) and Knutson and Ye (1987). Transfection efficiencies were determined by introducing 2 µg of an enhanced green fluorescent protein (eGFP) expression plasmid per $1 \times 10^7$ cells along with the test plasmids. The percent of eGFP-positive cells was determined by counting green cells using a UV microscope.

Transfection of 293/EBNA-1 cells was performed by plating $3 \times 10^5$ 293/EBNA-1 cells/well in a 6-well plate one day prior to transfection. For each well, 4 µg of each plasmid were mixed in 100 µL DMEM without FBS and, in parallel, 10 µL Polyfect were also mixed in 100 µL medium without FBS. Both solutions were combined and incubated at room temperature for 15 minutes. The cell growth medium was replaced with 800 µL DMEM without FBS and 200 µL of the DNA/Polyfect mixture were added to each well for 4-5 hours in a humidified incubator at 37° C. This transfection medium was then aspirated and replaced with 2 mL D10F per well. The next day, two identically transfected wells were transferred onto a 15 cm plate and grown under selection for at least two weeks with D10F with 220 µg/mL G418 sulfate.

Short-Term Replication Assay/Southern Blotting.

Extrachromosomal DNA was extracted and assayed by Southern blotting as described in Wang et al. (2006). Briefly, low molecular weight DNA was extracted from 1×10 Raji cells by alkaline lysis, and subsequently treated with phenol/chloroform and precipitated with ethanol. The precipitated DNA was resuspended in 1×TE and further treated with RNaseA and Proteinase K to digest contaminating RNA and protein, respectively. DNA was extracted with phenol/chloroform, precipitated with ethanol, and resuspended in distilled/deionized water. Ninety percent of the DNA was digested with a single-cut restriction endonuclease (e.g., MluI) to linearize the test and control plasmids and with DpnI to remove the unreplicated, bacterially-methylated input DNA. The remaining ten percent of the DNA was digested only with the linearizing restriction endonuclease. The DNA was subsequently concentrated by precipitation with ethanol and electrophoresed through a 0.8% agarose gel in 1×TAE buffer containing 500 ng/mL ethidium bromide at 30 V (2 V/cm) for 14-18 hours. The separated DNA fragments were nicked and denatured in situ, neutralized, and then transferred by capillary action to GeneScreen Plus membrane (NEN Life Sciences). Twenty-five ng of the parent vector backbone DNA was labeled using a RediPrime II kit (Amersham Biosciences) and purified with Quickspin columns (Roche). The blots were hybridized with the labeled probe in Ultrahyb (Ambion) at 42° C. for 16 hours or longer, extensively washed, and then exposed to a storage phosphor screen (Molecular Dynamics). Signals were visualized by a Storm 860 PhosphorImager, and band intensities were quantified by ImageQuant 5.2 (Molecular Dynamics).

Long-Term Replication Assay.

In order to measure the number of Raji cells in which transfected DNAs became established as plasmids, the percent of GFP-positive cells was determined three days post-transfection. These cell populations harboring the test plasmids were serially-diluted and plated in 96-well plates to contain a known number of green, transfected cells per well in 200 µL R10F+1 µg/mL puromycin. The number of puromycin-resistant colonies was counted after three weeks, and verified for continued colony viability after four weeks. The number of colony-free wells was used to calculate the colony formation efficiency by the Poisson distribution as follows:

Colony Formation Efficiency=[−ln(fraction of negative wells)]/number of transfected cells per well.

Competitive Electrophoretic Mobility Shift Assay (EMSA).

A competitive EMSA was conducted essentially as described in Wang et al. (2006). Briefly, 10 fmol of a double-stranded DNA probe containing one copy of a high-affinity, palindromic EBNA-1-binding site was end-labeled and incubated either in the absence or the presence of 20 mM dnEBNA-1/Softag1 and excess poly (dI*dC). Additional unlabeled competitor DNA containing wtDS, or one of the complete engineered origins (e.g., 2×(DS 1+2), 4×FRbs, 4×SiteIIIbs, 4×Rep*bs or S-W-W-S) was included in increasing concentrations from 1 to 14-fold EBNA-1-binding site excess. Competition for binding EBNA-1 by the unlabeled DNAs was analyzed by ImageQuant analysis of the bound and free probe bands as described for Southern blotting.

Chromatin-Immunoprecipitation (ChIP) Assay and Real-Time PCR Analysis.

For chromatin immunoprecipitation experiments, nuclei were prepared as described in Ritzi et al. (2003). For each sample $1 \times 10^7$ cells were harvested, washed with PBS and resuspended in 250 µL hypotonic buffer A (10 mM HEPES pH 7.9, 10 mM KCl, 1.5 mM $MgCl_2$, 0.34 M sucrose, 10% glycerol, 1 mM DTT, protease inhibitor mix Complete© (Roche)). Cells were lysed by adding 0.04% Triton X-100 and incubated for 10 minutes on ice. Samples were centrifuged (4 minutes, 1300×g, 4° C.) to separate soluble cytosolic and nucleosolic proteins from chromatin. Nuclei were washed at a concentration of $1 \times 10^8$ nuclei/ml in ice-cold buffer A supplemented with 200 mM NaCl. After centrifugation (1300×g, 5 minutes, 4° C.) nuclei were carefully resuspended in 1 mL buffer A. 9 mL pre-warmed buffer A supplemented with formaldehyde to a final concentration of 1.1% were added and the nuclei cross-linked for 5 minutes at 37° C. Fixed nuclei were washed twice with PBS/0.5% NP40, resolved in 2.7 mL LSB (10 mM HEPES pH 7.9, 10 mM KCl, 1.5 mM $MgCl_2$) and lysed by adding 300 µL 20% sarkosyl. The chromatin was transferred onto a 40 mL sucrose cushion (LSB plus 100 mM sucrose) and centrifuged (10 minutes, 4° C., 4000×g). Supernatant was removed and the chromatin was resuspended in 2 mL TE and sonicated (Branson sonifier 250-D, 35% amplitude, 2 minutes in 1 second intervals). For each immunoprecipitation, 500 µg of the nucleoprotein was adjusted with 1/10 volume of 11×NET (50 mM Tris, 150 mM NaCl, 0.5 M EDTA, 0.5% NP40). 10 µg of polyclonal rabbit antibodies directed against the human Orc2 protein or 50 µL hybridoma supernatant of the monoclonal EBNA-1-specific antibody 1H4 were added. The immunoprecipitation and purification of coprecipitated DNA was performed as described in Schepers et al. (2001). Real-time PCR analysis was performed according to the manufacturer's instructions using the same parameters and the primer pairs as described in Schepers et al. (2001). The primer pairs used were: origin forward, TCTTCAGCCACTGCCCTTGTG (SEQ ID NO:7); origin back, CAGATATCAAGCTTGTTAACCCT (SEQ ID NO:2); control forward, CACGACGGGGAGTCAGGC (SEQ ID NO:3); control back, GTAGCGGTG-GTTTTTTTGTTTGC (SEQ ID NO:4). The copy number of each test plasmid per cell for the ChIP experiments was determined by real-time PCR using a serial dilution of p3508 plasmid DNA as a standard. Input DNA from two independent experiments was digested with DpnI and 1, 10, and 100 ng of this total input DNA was used as a template for real-time PCR analysis.

Results

Engineering of EBNA-1-Dependent Origins of DNA Synthesis.

Figure 3A:
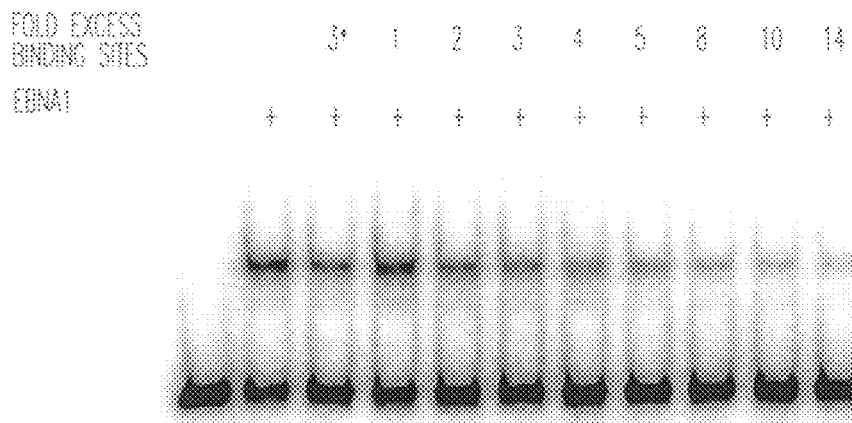
FIG. 3. The rank order of the affinity of EBNA1 for its binding sites in origins of DNA synthesis as determined by competitive EMSA. (A) Five fmol of end-labeled probe containing one EBNA 1-binding site from FR was incubated either in the absence or the presence of 1.6 nM dnEBNA1/Softag1 in a reaction volume of 25 µL at room temperature for 30 minutes. dnEBNA1/Softag1 is a derivative of the DNA-binding domain of EBNA1 fused to a defined epitope recognized by a murine monoclonal antibody (Thompson et al., 2003). Reactions contained increasing amounts (1 to 14-fold excess of binding sites) of unlabeled DNA fragments containing either wtDS or one of the engineered origins of DNA synthesis. Three-fold excess of wtDS EBNA-1-binding sites was included in one lane on all gels, marked with an asterisk, as an unlabeled competitor control and was used for sample normalization across experiments. Samples were electrophoresed through a 4% polyacrylamide gel at 300 V at 4° C. for 1.5-2 hours, dried onto Whatmann paper, exposed to a storage phosphor screen, and visualized by scanning on a Storm 640 PhospholImager. (B) The amount of competition for binding by EBNA-1 produced from each origin tested was normalized to the amount of competition for binding by EBNA-1 produced from a 3-fold excess of wtDS EBNA-1-binding sites. These values were plotted on the y-axis against the fold excess of unlabeled EBNA1-binding sites added to each reaction in order to determine the rank order of the affinity of EBNA-1 for all origins tested. Twenty-five-fold excess binding sites of the 4×Rep*bs containing DNA fragment was required to produce a similar amount of competition as 3-fold excess wtDS EBNA1-binding sites (data not shown). The rank order is: wtDS or 4×SiteIIIbs>2×(DS 1+2) or SWWS>>4×Rep*bs.
Figure 3B:
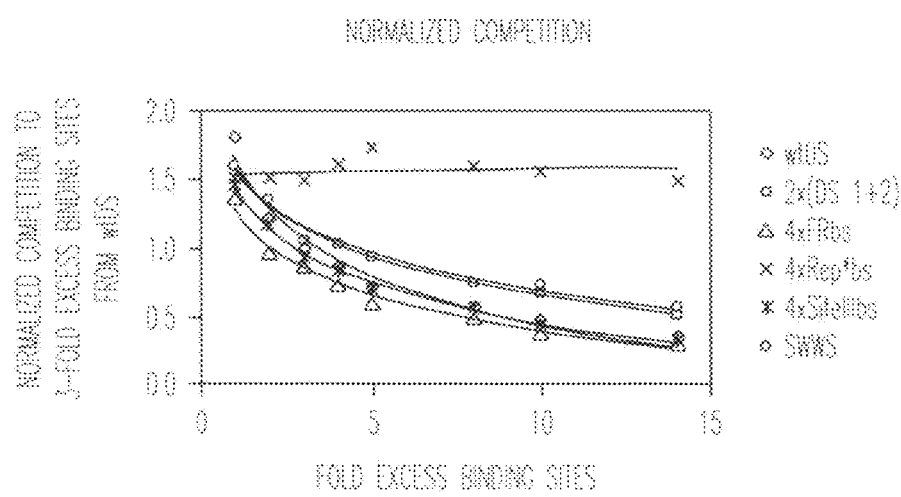
Figure 4:
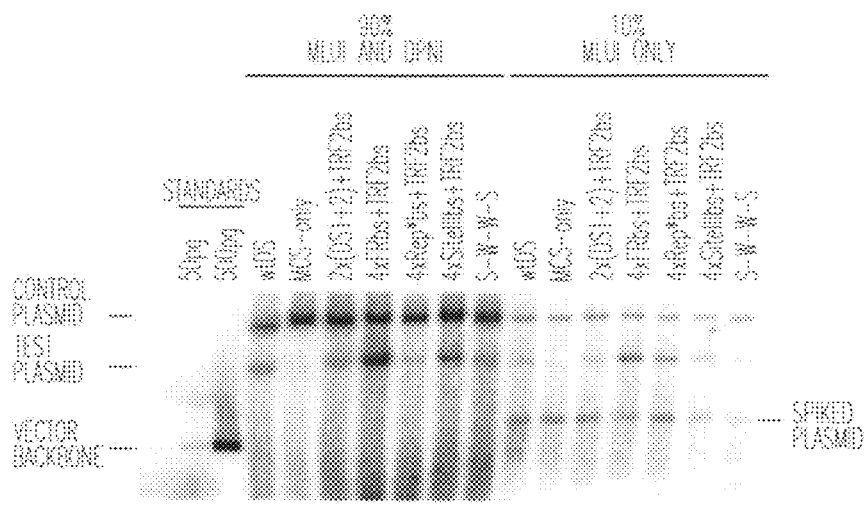
FIG. 4. The efficiency of the initiation of DNA synthesis from engineered origins containing TRF2-half-binding sites correlates with the affinity of EBNA1 for its origin-binding sites. Equal masses of the control plasmid (p3567) and of one of the test plasmids containing wtDS (p3487), the MCS-only (p3488), an origin with the flanking TRF2-half-binding sites (p3512-p3515) or the S-W-W-S origin (p3516) were electroporated into Raji cells. After 4 days, the extrachromosomal DNA was extracted from $1×10^7$ cells by alkaline lysis. Ninety percent of the samples was digested with both MluI and DpnI, and ten percent was digested with MluI only to linearize the DNA. To test the completeness of DpnI digestion, 5 ng of pPur plasmid was added as "spiked DNA" during extraction. For the analysis of this DNA, a Southern Blot using a radiolabeled probe produced by random priming of the pPUR vector backbone was hybridized to the electrophoresed and transferred DNAs. The identity of the test plasmid in each lane is given above it. As standards, 50 and 500 pg of linearized vector backbone were loaded on the left of the blot.

Many identified mammalian chromosomal origins of DNA synthesis are broad zones of initiation (for review, see Chapter 2 of DePamphilis (2006)), thus complicating any determination of their potential cis-acting elements. In order to define these requirements for discrete origins, 13 candidate origins of DNA synthesis modeled upon DS, with a range of different affinities for the initiator protein, EBNA-1, were engineered (FIG. 1). The rank order of the affinity of EBNA-1 for these engineered origins was compared directly by a competitive EMSA, in which each origin was used as unlabeled competitor DNA (FIG. 3). A comparison of the level of competition that each origin produced yielded the following rank order of affinity for EBNA-1:4×FRbs>wtDS or 4×SiteIIIbs>2×(DS 1+2) or SWWS>>4×Rep*bs. This ranking of affinities is consistent with the relative affinities of their individual EBNA-1-binding sites (Wang et al., 2006; Jones et al., 1989; Ambinder et al., 1990). The binding of the human TRF2 protein to DS increases the apparent affinity of EBNA-1 for this origin (Deng et al., 2002); therefore half-binding sites for TRF2 were incorporated into a subset of these engineered origins with the same arrangement for these half-binding sites as found in DS (FIG. 1). It was hypothesized that stabilizing the binding of TRF2 to the EBNA-1-dependent origins would enhance an origin's efficiency. To test this hypothesis, two origins, wtDS and 4×FRbs+TRF2hbs, were modified to contain one or two complete TRF2-binding sites in place of half-binding site(s) (FIG. 1).

The Affinity of EBNA-1 for its Binding to Candidate Origins with Binding Sites for TRF2 Correlates with their Efficiency of Initiating DNA Synthesis.

In order to determine whether the replicative efficiency of candidate origins of DNA synthesis correlates with the affinity of EBNA-1 for its origin binding sites, the 15 plasmids described above were scored for their ability to replicate shortly after introduction into EBV-positive B-cells. Raji cells (5×10$^6$ cells) were electroporated with 5 µg of an internal positive control plasmid (p3567), 5 µg of a test plasmid, and 1 µg of an eGFP-expression plasmid (p2134), and were cultured at appropriate cell-densities without selection for 4 days. Extrachromosomal DNA from 1×10$^7$ cells was then harvested by alkaline lysis, purified, and subsequently digested with either MluI alone or with MluI and DpnI. The digestion of this DNA was accomplished by two rounds of enzyme addition and was allowed to progress for at least 24 hours to ensure its completion. These DNAs were concentrated by precipitation with ethanol, and electrophoresed through a 0.8% TAE agarose gel, and subsequently detected by Southern Blotting. This assay measures the accumulation of DNAs synthesized during the 4 days following their introduction into the cells, and reflects their homing to those compartments that support DNA synthesis, their synthesis, and their maintenance in the proliferating cells.

The signal from the replicated, larger, positive-control plasmid (p3567) was present in all lanes and was used as a control for plasmid recovery, to normalize the signal of the replicated test plasmids, and to facilitate comparison between samples. Five nanograms of the pPUR vector backbone plasmid (Clontech) were also introduced prior to cell lysis to serve as an additional control for plasmid recovery and as a control for the completion of digestion with DpnI. The signal corresponding to this bacterially-methylated DNA is only present in those lanes containing 10% of the total sample that has only been linearized by digestion with MluI so long as the digestion with DpnI in the other samples was complete.

Both the larger (p3567) and smaller (p3487) positive-control oriP plasmids replicated efficiently, and consistently produced 40-100 replicated plasmids per transfected cell detected 4 days post-electroporation. In addition, a plasmid with wtDS reintroduced into the MCS of p3488 replicated indistinguishably from the other positive control plasmids (data not shown). The MCS-only (p3488) plasmid produced signals indistinguishable from background when quantified with ImageQuant 5.2 (Molecular Dynamics). In all cases, the candidate origins of DNA synthesis engineered to contain half-binding sites for TRF2 (p3512-p3515) replicated more efficiently than did the comparable origins lacking them (p3508-p3511) (compared in Table 1). Signals arising from the replicated test plasmids were normalized to the signal from the positive control oriP plasmid, which was set at 100%.

Unexpectedly, the origin composed of four high-affinity EBNA-1-binding sites from FR with flanking TRF2-half-binding sites (p3513) supported DNA replication 220% as efficiently as did wtDS. In comparison, the origins composed of two pairs of medium-affinity EBNA-1-binding sites from DS (p3512) or Site III (p3515) with TRF2-half-binding sites flanking them replicated 57% and 86% as efficiently as did wtDS, respectively. The origin composed of four pairs of the slightly lower affinity EBNA-1-binding site from Rep* with TRF2-half-binding sites flanking them (p3514) replicated only 28% as efficiently as did wtDS. In contrast to these origins that are flanked by TRF2-half-binding sites, the same origins lacking them replicated much less efficiently in all cases. The origin composed of 4 EBNA-1-binding sites from FR (p3509) replicated 12% as efficiently as did wtDS, and was not significantly different from the origin composed of two pairs of EBNA-1-binding sites from DS, which replicated 15% as efficiently as wtDS. However, the candidate origin composed of 4 EBNA-1-binding sites from Rep* did not produce a detectable signal. Among the derivatives without half-sites for TRF2, two replicated better than the FR and DS-derived origins lacking those half-sites. The origin composed of 4 medium-affinity EBNA-1-binding sites derived from Site III replicated at 27% the efficiency of wtDS. Finally, the hybrid origin created from EBNA-1-binding sites derived from both FR and Site III (S-W-W-S, p3516) replicated at 61% the efficiency of wtDS. This result is interesting because the arrangement of 'strong' and 'weak' EBNA-1-binding sites, as found in wtDS, replicated more efficiently than did the related candidate origins composed of four of the 'strong' (p3509, 4×FRbs) or 'weak' (p3511, 4×SiteIII) EBNA-1-binding sites. This result indicates that not only the affinities of binding sites for a replicator, but also their arrangement, can be determinants of the efficiency of that origin.

TABLE 1

Comparison of the short-term replication efficiencies of the natural and artificial origins of DNA synthesis in Raji cells.

| Plasmid # | Origin Description | Normalized Replicative Efficiency | Standard Deviation |
|---|---|---|---|
| 3487 | wtDS | 1 | N/A |
| 3488 | MCS-only | 0.03 | 0.04 |
| 3508 | 2 × (DS 1 + 2) | 0.15 | 0.06 |
| 3509 | 4 × FRbs | 0.12 | 0.08 |
| 3510 | 4 × Rep*bs | 0.001 | 0.01 |
| 3511 | 4 × SiteIIIbs | 0.27 | 0.01 |
| 3516 | S-W-W-S | 0.61 | 0.19 |
| 3512 | 2 × (DS 1 + 2) + TRF2(½, ½, ½) | 0.57 | 0.28 |
| 3513 | 4 × FRbs + TRF2(½, ½, ½) | 2.20 | 0.60 |
| 3514 | 4 × Rep*bs + TRF2(½, ½, ½) | 0.28 | 0.09 |
| 3515 | 4 × SiteIIIbs + TRF2(½, ½, ½) | 0.86 | 0.10 |
| 3591 | wtDS + TRF2(½, ½, 1) | 1.7 | 0.65 |
| 3592 | 4 × (FRbs) + TRF2(½, ½, 1) | 0.73 | 0.03 |
| 3603 | wtDS + TRF2(1, ½, 1) | 1.77 | 0.92 |
| 3604 | 4 × (FRbs) + TRF2(1, ½, 1) | 0.92 | 0.33 |

In comparing these two classes of engineered origins, it was observed that the presence of TRF2-half-binding sites flanking the EBNA-1-binding sites increased the efficiency of the initiation of DNA synthesis differently for different origins. Moderate increases in replicative efficiency were observed for the DS and Site III-derived origins (3.8 and 3.2-fold increases, respectively). However, more dramatic increases were observed for the Rep*-derived origin, which supported detectable replicative signals in the presence of TRF2-half-binding sites but not in their absence, and for the FR-derived origin (a 18.4-fold increase). Surprisingly, the 4×FRbs+TRF2hbs origin (p3513) initiated DNA synthesis 2.2-fold more efficiently than did wtDS. This finding indicates that EBV has evolved to use a sub-maximally efficient origin of DNA synthesis as its latent origin.

Next it was tested whether complete TRF2-binding sites would further enhance the efficiency of DNA replication with the notion that increasing the affinity of TRF2 dimers for candidate origins would increase the apparent affinity of EBNA-1 for them. The wtDS and 4×FRbs+TRF2hbs origins were modified to introduce one or two complete TRF2-binding sites in the place of the flanking half-binding sites, and slight differences were found in their effect, for instance, including one complete TRF2-binding site to wtDS (p3591) enhanced its replicative efficiency slightly (170% of wtDS) while inclusion of two such binding sites (p3592) inhibited origin function slightly (73% of wtDS). Similar constructions with 4×FRbs+TRF2hbs (p3603, p3604) increasingly inhibited origin function (78% and 33% of 4×FRbs+TRF2hbs, respectively).

The Affinity of EBNA-1 for Binding to Candidate Origins with Binding Sites for TRF2 is a Major Determinant of Establishment of Extrachromosomal Replicons.

EBV-derived plasmid replicons that are introduced into mammalian cells must proceed successfully through a process termed 'establishment' in order to be stably replicated and maintained (Leight and Sugden, 2001). Newly introduced plasmids are rapidly lost from the cell population at about 15-25% per cell generation for approximately two weeks. Subsequently, the plasmids that remain are lost from the population at a rate of 3-4% and are said to be 'established' in the cell population. Little is known mechanistically of how establishment occurs.

In order to determine if the affinity of EBNA-1 for its origin-binding sites has an effect upon the establishment of plasmids, the plasmids bearing either a natural or an engineered origin of DNA synthesis were scored for their ability to form colonies in a long-term replication assay. Briefly, 5×10 Raji cells were electroporated and were cultured at appropriate cell-densities for 3 days. At this time, the efficiency of electroporation for each introduced plasmid was determined by measuring the percent of GFP-positive cells present in the population. These cell populations harboring the test plasmids were serially diluted and aliquoted into 96-well plates so that a known number (between 1-10,000) of GFP-positive cells were present per well. This range allowed the growth of cells for all plasmids bearing an origin of DNA synthesis three weeks post-electroporation, enabling an accurate comparison of the efficiencies of colony formation of each plasmid after growth under selection with puromycin.

The efficiency of long-term colony formation depends on the efficiency of establishment; 1-10% of cells transfected or electroporated with plasmids bearing wtDS can give rise to colonies (Wang et al., 2006; Leight and Sugden, 2001) (C. Wang, unpublished results). The efficiency of colony formation of cells with the plasmid bearing wtDS (p3487) in these experiments (8.2%) is consistent with that in previous reports. The efficiencies of colony formation of cells with the plasmids bearing no origin or one of the engineered, candidate origins of DNA synthesis were normalized to the efficiency of cells with wtDS, and are compared in Table 2. The cells bearing the MCS-only (p3488) plasmid yielded no colonies, and hence the background efficiency of colony formation was set to be less than 1 in 10,000, or <0.056% overall and <0.68% of the efficiency of wtDS. The origins lacking TRF2-binding sites generally were established quite inefficiently (e.g., <1.7%-5% of wtDS). In contrast, the one origin constructed with binding sites from both FR and Site III and having the same arrangement of sites with different affinities for binding EBNA-1 as found in DS (S-W-W-S, p3516) was more efficient at supporting the formation of colonies (17.4% that of cells with wtDS) than either of the related candidate origins composed solely of binding sites from FR or Site III (p3509, p3511).

TABLE 2

Comparison of the efficiencies of colony formation of the natural or artificial origins of DNA synthesis in Raji cells.

| Plasmid # | Origin Description | Normalized Replicative Efficiency |
|---|---|---|
| 3487 | WtDS | 1 |
| 3488 | MCS-only | <0.007 |
| 3508 | 2 × (DS 1 + 2) | 0.051 |
| 3509 | 4 × FRbs | <0.017 |
| 3510 | 4 × Rep*bs | <0.017 |
| 3511 | 4 × SiteIIIbs | 0.051 |
| 3516 | S-W-W-S | 0.174 |
| 3512 | 2 × (DS 1 + 2) + TRF2(½, ½, ½) | 0.406 |
| 3513 | 4 × FRbs + TRF2(½, ½, ½) | 6.21 |
| 3514 | 4 × Rep*bs + TRF2(½, ½, ½) | 0.014 |
| 3515 | 4 × SiteIIIbs + TRF2(½, ½, ½) | 1.88 |
| 3591 | wtDS + TRF2(½, ½, 1) | 1.51 |

TABLE 2-continued

Comparison of the efficiencies of colony formation of the natural or artificial origins of DNA synthesis in Raji cells.

| Plasmid # | Origin Description | Normalized Replicative Efficiency |
|---|---|---|
| 3592 | 4 × (FRbs) + TRF2(½, ½, 1) | 0.370 |
| 3603 | wtDS + TRF2(1, ½, 1) | 4.68 |
| 3604 | 4 × (FRbs) + TRF2(1, ½, 1) | 3.13 |

The addition of the TRF2-half-binding sites to these origins had a significant effect on the efficiencies of colony formation for all origins tested. The 2×(DS 1+2)+TRF2hbs (p3512) origin formed colonies 40.6% as efficiently as wtDS, resulting in about 8-fold increase over the identical origin that lacked the TRF2-half-binding sites. The inclusion of TRF2-half-binding sites to 4×FRbs (p3513), 4×Rep*bs (p3514) and 4×SiteIIIbs (p3515) resulted in even more striking increases in the efficiency of colony formation relative to these mediated by the related candidate origins lacking those sites. The 4×SiteIIIbs+TRF2hbs origin supported colony formation 1.88-fold better than did wtDS, or about 37-fold better than the same origin lacking TRF2-half-binding sites (p3511). Moreover, introduction of TRF2-half-binding sites to the 4×FRbs and 4×Rep*bs origins supported detectable levels of colony formation, whereas in their absence no colonies were observed above background. The 4×FRbs+TRF2hbs origin functioned significantly better than wtDS in forming colonies (e.g., 6.2-fold increase). Thus, EBV has been selected to have a sub-maximally efficient origin for the establishment of its plasmids, which is consistent with the findings of the short-term replication assays.

The modification of the half-binding sites for TRF2 in wtDS and 4×FRbs+TRF2hbs to create one or two complete TRF2-binding sites flanking the EBNA-1-binding sites also affected the efficiency of colony formation of these origins. Similar to what was observed in the short-term assay, the wtDS origin with one complete TRF2-binding site supported colony formation slightly better than wtDS (150% of wtDS), while inclusion of two such binding sites inhibited efficiency of colony formation (37% of wtDS). The inclusion of complete TRF2-binding sites to the 4×FRbs+TRF2hbs origin increasingly inhibited colony formation (75% and 50% of 4×FRbs+TRF2hbs, respectively).

The Presence of Binding Sites for TRF2 Correlates with Increased Binding of EBNA-1 and ORC2 In Vivo at Candidate Origins Having found that candidate origins with binding sites for TRF2 supported replication in proportion to their affinities for binding of EBNA-1 as measured in vitro, it was determined whether the binding of EBNA-1 and ORC2 in vivo was also in proportion to their support of replication. The levels of binding EBNA-1 and ORC2 were assayed using chromatin immunoprecipitation (ChIP) with antibodies to EBNA-1 and ORC2 and 293/EBNA-1 cells carrying the introduced plasmids with the candidate origins. These cells do not have endogenous EBV as do Raji cells that might confound the ChIP assays. The levels of the plasmid DNAs in all of the studied samples were measured by real-time PCR and found to be similar (Table 3). The levels of EBNA-1 and ORC2 bound to the candidate origins and to a distal DNA common to all the plasmids were determined by measuring the differences between the amount of those DNAs precipitated by an antibody specific to EBNA-1 or ORC2 and that precipitated by an isotype control antibody. The five origins with binding sites for TRF2 bound on average two times the levels of EBNA-1 and four times the level of ORC2 as did the three lacking those binding sites, as measured in vivo.

TABLE 3

Comparison of the association of ORC2 and EBNA1 with the engineered origins of DNA synthesis after establishment in 293/EBNA1 cells. The $\log_2$ values given denote the difference in Ct (cycle threshold) values between DNA fragments containing the test origin or a distal control region on the plasmid when immunoprecipitated with a specific antibody to ORC2 or EBNA1 and the observed signal when immunoprecipitated with an isotype control antibody. The cycle threshold value is the cycle at which the signal rises above the background.

| Plasmid # | Origin Description | ORC2 origin | EBNA1 origin | ORC2 control | EBNA1 control | Average Plasmid # per Cell |
|---|---|---|---|---|---|---|
| 3487 | wtDS | 6.2 +/− 1.0 | 8.8 +/− 0.4 | 0.4 +/− 0.2 | 0.9 +/− 0.1 | 41.3 +/− 5.7 |
| 3508 | 2 × (DS 1 + 2) | 3.9 +/− 0.6 | 7.4 +/− 0.9 | 0.8 +/− 0.4 | 1.1 +/− 0.1 | 32.0 +/− 3.6 |
| 3511 | 4 × SiteIIIbs | 3.7 +/− 0.5 | 6.0 +/− 0.7 | 0.7 +/− 0.3 | 1.1 +/− 0.3 | 31.0 +/− 6.9 |
| 3516 | S-W-W-S | 3.7 +/− 0.6 | 6.9 +/− 0.3 | 0.4 +/− 0.2 | 0.8 +/− 0.3 | 31.3 +/− 3.5 |
| 3512 | 2 × (DS 1 + 2) + TRF2(½, ½, ½) | 5.4 +/− 0.3 | 7.9 +/− 0.5 | 0.7 +/− 0.4 | 0.4 +/− 0.3 | 34.3 +/− 4.7 |
| 3513 | 4 × FRbs + TRF2(½, ½, ½) | 5.6 +/− 0.4 | 7.9 +/− 0.4 | 0.3 +/− 0.3 | 0.5 +/− 0.3 | 35.7 +/− 5.5 |
| 3514 | 4 × Rep*bs + TRF2(½, ½, ½) | 6.0 +/− 1.0 | 6.9 +/− 0.7 | 0.5 +/− 0.4 | 0.7 +/− 0.1 | 38.0 +/− 4.0 |
| 3515 | 4 × SiteIIIbs + TRF2(½, ½, ½) | 6.4 +/− 0.9 | 7.5 +/− 0.9 | 0.8 +/− 0.4 | 1.4 +/− 0.4 | 38.3 +/− 4.2 |

Discussion

Previous studies of DS and Rep*, two latent origins of DNA synthesis of EBV, have uncovered shared properties that contribute significantly to their replicative function. It was determined if one of these features, EBNA-1's affinity for its binding sites in the origin of DNA synthesis, affected the efficiency of the replication of plasmids bearing them. To this end, several plasmids were constructed that contained candidate origins of DNA synthesis composed of EBNA-1-binding sites with a range of different affinities and introduced into human B-cells. These EBNA-1-dependent origins of DNA synthesis were designed to mimic the arrangement of the EBNA-1 and TRF2-half-binding sites found in DS. Some of these constructed plasmids produced robust replicative signals in both short and long-term replication experiments and permitted the comparison of the replicative efficiencies of the various candidate origins. From this study, there are at three general findings: 1) there is a direct correlation between EBNA-1's affinity for an origin containing TRF2-half-binding sites and its frequency of supporting the initiation of DNA synthesis; 2) there is a direct correlation between EBNA-1's affinity for an origin containing TRF2-half-binding sites and the frequency of establishment of a plasmid; 3) half-binding sites for TRF2 increase on average the levels of EBNA-1 and ORC2 bound to origins in vivo.

Figure 5:
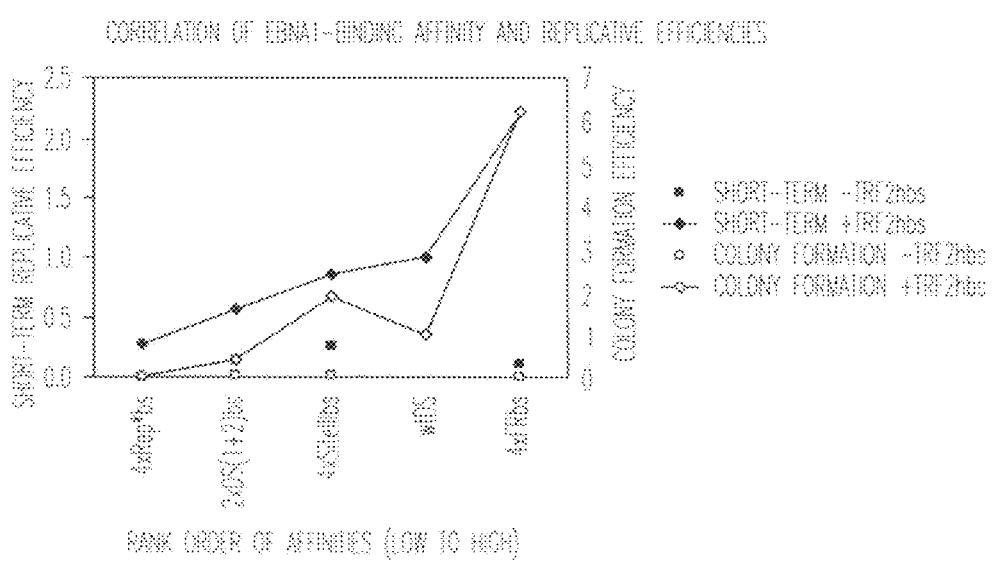
FIG. 5. A graphical representation of the correlation of EBNA1-binding affinity for its origin binding sites in the presence and absence of TRF2-half-binding sites with measured replicative efficiencies. The rank order of affinities of EBNA1-binding sites are placed on the x-axis, from weakest to strongest (left to right); the replicative efficiencies in the short-term assay (from Table 1) and the colony formation assay (from Table 2) are placed on the left and right y-axes, respectively. A positive correlation between the affinity of EBNA1 for its origin binding sites with both replicative efficiencies is observed in the presence of TRF2-half-binding sites, but not in their absence. The replicative efficiencies of wtDS lacking the TRF2-half-binding sites were not determined in these assays, and are omitted from this graph.

A comparison of the efficiencies by which these engineered origins initiate DNA synthesis to that of wtDS at four days post-electroporation yielded several unexpected findings (Table 1). First, EBNA-1's affinity for its binding different sites in engineered origins correlated with the origins' efficiency in supporting the initiation of DNA synthesis in the presence of TRF2-half-binding sites, but not in the absence of TRF2 half-binding sites (Kendall's rank correlation test, p=0.021) (depicted graphically in FIG. 5). Second, the origin with 4×FRbs+TRF2hbs (p3513) initiated DNA synthesis 2.2-fold more efficiently than did wtDS. The EBV genome therefore uses a less than maximally efficient origin of DNA synthesis during its latent phase of its life cycle. It is known that imperfections in the synthesis and partitioning of EBV's genome are balanced to generate a wide distribution in the numbers of viral plasmids per cell (Nanbo et al., 2007). This balance is achieved in part by synthesis and partitioning being mechanistically coupled (Nanbo et al., 2007) and allows the viral replicon with minimal requirements to be maintained stably in cells to which it provides a selective advantage. Thus, DS is likely tailored to foster EBV's successful lifestyle.

A third finding from the short-term replication assay was the magnitude of the effect produced by TRF2-half-binding sites flanking the pairs of EBNA-1-binding sites. When the TRF2-half-binding sites were present in the origins with 2×(DS 1+2) (p3512) and 4×SiteIIIbs (p3514), they supported a 3.6 and 3.2-fold increase in the efficiency of initiating DNA synthesis relative to the same origins lacking them (p3508 and p3511, respectively). Even more strikingly though was the 18.4-fold effect observed with the origin with 4×FRbs+ TRF2hbs (p3513) when compared to the same origin lacking the TRF2-half-binding sites (p3509). These findings indicate that TRF2 contributes more to the initiation of DNA synthesis at EBNA-1-dependent origins than previously appreciated. Further characterization of the mechanism of TRF2's stimulation of the initiation of DNA synthesis is therefore warranted.

When these engineered origins were introduced into Raji cells and selected with puromycin for three weeks, a similar trend (depicted graphically in FIG. 5) in the efficiencies of colony formation of these origins was found as determined by Kendall's rank correlation test (p=0.035). All plasmids bearing origins of DNA synthesis that contained TRF2-half-binding sites formed colonies more efficiently than the same plasmids lacking them. The inclusion of flanking TRF2-binding sites had a similar effect on both the initiation of DNA synthesis and the formation of colonies, as did the affinity of EBNA-1 for its origin binding sites. However, when TRF2-half-binding sites were absent from the candidate origins, the affinity of EBNA-1 for its origin binding sites alone was not a determinant of the replicative efficiency. The hybrid S-W-W-S origin (p3516) replicated better in both the short and long term than either candidate origin with the same EBNA-1-binding sites (4×FRbs, p3509; 4×SiteIIIbs, p3511). This finding is in agreement with previous studies of 8×Rep*, which replicates as well as wtDS with 8 pairs of low-affinity EBNA-1-binding sites in the absence of TRF2-half-binding sites (Wang et al., 2006). It indicates that the relative positioning of distinct binding sites for EBNA-1 can also be a determinant of the efficiency of engineered origins.

These data lead to two new interpretations of this well-studied model replicon. First, EBNA-1's affinity for an origin may affect some function(s) in addition to the initiation of DNA synthesis. Potentially, a higher affinity of EBNA-1 for its origin-binding sites could stimulate the homing of the introduced plasmids to the replication-competent compartments of the cell, thus allowing a higher percentage of the plasmids to begin replicating in the initial S-phases. Alternatively, higher affinity EBNA-1-binding sites present in the origin of DNA synthesis may act cooperatively with those sites of FR to stimulate FR's beneficial effects upon plasmid duplication. Second, the present data indicates that EBNA-1's affinity for an origin is one major determinant of the efficiency of establishment of that origin. Additionally, it is clear that the association of TRF2 with an origin of DNA synthesis plays a substantial role in this process as well. However, the mechanism(s) by which TRF2 stimulates the initiation of DNA synthesis and the establishment of plasmids is/are unclear. If TRF2 were only stimulating the initiation of DNA synthesis by increasing the apparent affinity of EBNA-1 for its binding sites in an origin, then sites bound by EBNA-1 with the highest affinity should be least affected. However, this inverse correlation was neither observed in short or long-term replication assays, nor in the ChIP measurements in vivo. Thus, activities of TRF2 other than its cooperative binding with EBNA-1 likely stimulate the replication of the test plasmids. TRF2 has also been shown to interact via its N-terminal basic domain with the bromo adjacent homology (BAH) domain of ORC1 (Atanasiu et al., 2006). This domain on ORC1 has been implicated as being important for the replication of oriP plasmids (Noguchi et al., 2006). Derivatives of TRF2 with a deletion of its N-terminal basic domain or with a point mutation within it (E111K), for example, inhibit the recruitment of ORC1 to DS and the replication of oriP plasmids (Noguchi et al., 2006). The contribution of TRF2-binding sites to replication may therefore reflect the synergistic effects of an increased affinity of EBNA-1 for its origin binding sites and the enhanced recruitment of ORC to the origin. This explanation is supported by the present finding that the presence of half-binding sites for TRF2 at test origins correlates with increased binding by both EBNA-1 and ORC2 in vivo.

A model consistent with the present findings posits that structural differences in either the DNA or EBNA-1 are caused by differences in EBNA-1's interaction with the different bases of the binding sites it binds with different affinities. This type of differential interaction has been previously shown with the trp repressor binding to sites where the central two base pairs of the full binding site differ. An alteration of the dinucleotide between the half-sites for binding did not significantly affect the stability of the trp repressor binding to the primary, full binding site (Bareket-Samish et al., 1997). However, the assembly of additional trp repressors at two half-sites flanking the full binding site was greatly affected (Bareket-Samish et al., 1997). This effect of differential binding of a primary binding site, which affects the recruitment and loading of additional repressor molecules to flanking half-sites, has been implicated as the mechanism for differential repression of the various trp operators. Based upon this model, the differences in the overall EBNA-1/DNA structure may affect the positioning, recruitment, and/or loading of TRF2 to its flanking half-sites, as well as other cellular replicative factors such as the members of the pre-Replicative Complex (pre-RC). This EBV-derived model system permits further analysis of what trans-acting factor(s) are necessary and/or sufficient for affecting the efficiency of initiation of DNA synthesis in concert with the cis features identified herein.

REFERENCES

Altmann et al., *Proc. Natl. Acad. Sci. U.S.A.*, 103:14188 (2006).
Ambinder et al., *J. Virol.* 64:2369 (1990).
Atanasiu et al., *EMBO Rep.*, 7:716 (2006).
Baer et al., Nature, 310:207 (1984).
Bareket-Samish et al., *J. Mol. Biol.*, 267:103 (1997).
Bashaw and Yates, *J. Virol.*, 75:10603 (2001).).
Chaudhuri et al., *Proc. Natl. Acad. Sci. U.S.A.*, 98:10085 (2001).
Chittenden, *J. Virol.* 63:3016 (1989).
Deng et al., *J. Virol.*, 77:11992 (2003).
Deng et al., *Mol. Cell*, 9:493 (2002).
DePamphilis, DNA replication and human disease, Cold Spring Harbor monograph series; 46, Cold Spring Harbor Laboratory Press, Cold Spring Harbor, N.Y. (2006).
Dhar et al., *Cell*, 106:287 (2001).
Dubensky et al., *Proc. Natl. Acad. Sci. U.S.A.*, 81:7529 (1984).
Evens et al., *Gene Ther.*, 4:264 (1997).
Felgner et al., *Nature*, 337:387 (1989).
Gahn, *Cell*, 58:527 (1989).
Harrison, *J. Virol.*, 68:1913 (1994).
Henning et al., *Cell*, 82:555 (1995).
Hirai et al., *Biochem. Biophys. Res. Commun.*, 241:112 (1997).
Hung et al., *Proc. Natl. Acad. Sci. U.S.A.*, 98:1865 (2001).
Jones et al., *J. Virol.* 63:101 (1989).
Julien et al., *Virology*, 326:317 (2004).
Kaneda, *Mol. Urol.*, 5:85 (2001).
Kirchmaier and Sudgen, *J. Virol.*, 72: 4657 (1998)
Kirchmaier et al., *J. Virol.*, 69:1280 (1995).
Knutson and Yee, *Anal. Biochem.*, 164:44 (1987).
Koons, *J. Virol.*, 75:10582 (2001).
Kreppel, *J. Virol.*, 78:9 (2004).
Langle-Rouault et al., *J. Virol.*, 72:6181 (1998).
Legerski et al., *Nature*, 360:610 (1992).
Lei et al., *Gene Ther.*, 3:427 (1996).
Leight and Sugden, *Mol. Cell. Biol.*, 21:4149 (2001).
Leight et al., *J. Virol.* 75:10709 (2001).
Levitskaya et al., *Proc. Natl. Acad. Sci. U.S.A.*, 94:12616 (1997).
Lupton, *Mol. Cell. Biol.*, 5:2533 (1985).
Magin-Lachmann, *BMC Biotechnol.*, 3:2 (2003).
Mautner et al., *Oncogene*, 12:1299 (1996).
Mazda, *Curr. Gene Ther.*, 2:379 (2002).
Menezes et al., *Biomedicine*, 22:276 (1975).
Moran et al., *Cell*, 87:917 (1996).
Nanbo et al., *Embo J.* 26:4252 (2007).
Niller et al., *J. Biol. Chem.*, 270:12864 (1995).
Noguchi et al., *EMBO J.* 25:5372 (2006).
Perales et al., *Proc. Natl. Acad. Sci. U.S.A.*, 91:4086 (1994).
Peterson et al., *Gene*, 107:279 (1991).
Polonskaya et al., *Virology*, 328:282 (2004).
Pulvertaft, *J. Clin. Pathol.*, 18:261 (1965).
Rawlins et al., *Cell*, 42:859 (1985).
Ren, *Stem Cells*, 24:1338 (2006).
Ritzi et al., *J. Cell Sci.* 116:3971 (2003).
Schepers et al., *EMBO J.*, 20:4588 (2001).
Schepers et al., *EMBO J.* 20:4588 (2001).
Sears et al., *J. Virol.*, 78:11487 (2004).
Simpson et al., *Mol. Cell. Biol.*, 16:5117 (1996).
Stanfield-Oakley et al., *J. Mol. Biol.*, 256:503 (1996).
Thompson et al., *Anal. Biochem.*, 323:171 (2003).
Wang et al., *Mol. Cell. Biol.*, 26:1124 (2006).
White, *J. Virol.*, 75:11249 (2001).
Williams, *J. Virol.*, 67:2707 (1993).
Wolff et al., *Science*, 247:1465 (1990)
Wolgemuth et al., *Gene Ther.*, 3:503 (1996).
Wysokenski, *J. Virol.*, 63:2657 (1989).
Yates et al., *J. Virol.*, 74:4512 (2000).
Yates et al., *Proc. Natl. Acad. Sci. U.S.A.*, 81:3806 (1984).

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A recombinant vector comprising a DNA segment having a synthetic origin of DNA synthesis that binds EBNA-1, which synthetic origin of DNA synthesis when present in the vector in a cell that expresses EBNA-1, is capable of enhanced initiation efficiency of DNA synthesis of sequences linked to the synthetic origin of DNA synthesis and maintenance of the linked sequences relative to a corresponding wild-type origin of DNA synthesis with two pairs of binding sites for EBNA-1, the pairs flanked and separated by a half-binding binding site for TRF2, wherein the synthetic origin of DNA synthesis comprises at least two pairs of binding sites for EBNA-1 that are flanked and separated by at least a half-binding site for TRF2, wherein the synthetic origin has more half-binding sites for TRF2 than the corresponding wild-type origin of DNA synthesis or has FR binding sites, Rep* binding sites or Site III binding sites, or a combination thereof.

2. The recombinant vector of claim 1 wherein the two EBNA-1 binding sites in a pair have 21 by center to center spacing.

3. The recombinant vector of claim 1 wherein the synthetic origin consists of four binding sites for EBNA-1 and three half-binding sites for TRF2.

4. The recombinant vector of claim 1 wherein the synthetic origin has two half-binding sites for TRF2 in opposite orientation.

5. The recombinant vector of claim 1 wherein the two pairs of EBNA-1 binding sites in the synthetic origin are flanked on one end by one half-binding site for TRF2 and on the other end by two tandem half-binding sites for TRF2, wherein the two tandem half-binding sites for TRF2 are in the same orientation and in the opposite orientation relative to the one half-binding site for TRF2.

6. The recombinant vector of claim 1 wherein two half-binding sites for TRF2 in the synthetic origin are in the same orientation.

7. The recombinant vector of claim 1 wherein the two pairs of EBNA-1 binding sites in the synthetic origin are flanked on one end by one half-binding site for TRF2 and on the other end by two tandem half-binding sites for TRF2, wherein the two half tandem half-binding sites for TRF2 are in the same orientation as the one half-binding site for TRF2.

8. The recombinant vector of claim 1 wherein the EBNA-1 binding sites in the synthetic origin include DS binding sites.

9. The recombinant vector of claim 1 wherein the EBNA-1 binding sites in the synthetic origin include FR binding sites.

10. The recombinant vector of claim 1 wherein the EBNA-1 binding sites in the synthetic origin include Rep* binding sites.

11. The recombinant vector of claim 1 wherein the EBNA-1 binding sites in the synthetic origin include Site III binding sites.

12. The recombinant vector of claim 1 wherein the synthetic origin consists of four EBNA-1 binding sites.

13. The recombinant vector of claim 12 wherein the sequence of at least two of the EBNA-1 binding sites is the same.

14. The recombinant vector of claim 1 wherein one of the EBNA-1 binding sites includes the sequence GG/AT/AAG/AT/CAT/CA/GTA/G/CCTAC/TC/T (SEQ ID NO:20).

15. The recombinant vector of claim 1 wherein one of the EBNA-1 binding sites includes the sequence GATAG-TATATACTACT (SEQ ID NO:21) or GGAAGCATATGC-TACC (SEQ ID NO:22).

16. The recombinant vector of claim 1 wherein one of the EBNA-1 binding sites includes the sequence GATAGCATAT-GCTACC (SEQ ID NO:23).

17. The recombinant vector of claim 1 wherein one of the EBNA-1 binding sites includes the sequence GGAAATACGTCCTACC (SEQ ID NO:24).

18. The recombinant vector of claim 1 wherein one of the EBNA-1 binding sites includes the sequence GGTAATA-CATGCTATC (SEQ ID NO:25).

19. The recombinant vector of claim 1 wherein one of the EBNA-1 binding sites includes the sequence GGA/GA/C/TAA/GC/TA/CC/TA/G/TC/TA/GCC/TA/G/T (SEQ ID NO:26), or 16 contiguous nucleotides of (SEQ ID NO:27)
GGA/GA/C/TAA/GC/TA/CC/TA/G/TC/TA/GCC/TA/G/TC/TCC, (SEQ ID NO:28)
GA/GA/C/TAA/GC/TA/CC/TA/G/TC/TA/GCC/TA/G/TC/TCC
or (SEQ ID NO:29)
GGA/GA/C/TAA/GC/TA/C/GA/CC/TA/G/TC/TA/GC/TC/TA/G/T/CTC.

20. The recombinant vector of claim 1 wherein one of the EBNA-1 binding sites includes the sequence NGGA/

GTAGC/TA/CT (SEQ ID NO:30), T/C/GC/G/TG/AA/GA/ TAG/AC/TAT (SEQ ID NO:31), wherein N=A, T, C or G.

21. The recombinant vector of claim 1 wherein one of the EBNA-1 binding sites includes the sequence T/G/CG/T/AG/ AA/GC/TAG/AC/T/GA/CT/C/G (SEQ ID NO:32).

22. The recombinant vector of claim 1 wherein one of the EBNA-1 binding sites has the sequence A/TC/GGATAGCA/ T/G/CT/A/CG (SEQ ID NO:33).

23. The recombinant vector of claim 1 wherein one of the EBNA-1 binding sites has the sequence GRHAVNNNNNVYTDYY (SEQ ID NO:34), wherein R is G or A, Y is T or C, V is A, G or C, H is A, T or C, D is A, T or G and N is A, T, G, or C.

24. The recombinant vector of claim 1 wherein one of the TRF2 half-binding sites has the sequence TTAGGGTTA, GGGTTA, TAACCC or TAACCCTAA.

25. The recombinant vector of claim 1 further comprising one or more expression cassettes each of which encodes one or more gene products.

26. The recombinant vector of claim 1 further comprising a DNA segment which encodes a noncytotoxic derivative of a wild-type protein from a lymphotrophic herpes virus which corresponds to EBNA-1 of Epstein-Barr virus (EBV), which derivative activates transcription at levels at least 5% that of the corresponding wild-type protein from an extrachromosomal template after the derivative binds a DNA sequence in the extrachromosomal template which is capable of binding the wild-type protein with an affinity that is at least 10% that of the binding of the wild-type protein to a DNA sequence which corresponds to oriP of EBV, which derivative lacks sequences present in the corresponding wild-type protein that activate transcription from an integrated template, and which derivative has a nuclear localization sequence and at least three consecutive tripeptides including Gly-Gly-Ala, Gly-Ala-Gly, Gly-Gly-Gly, Ala-Gly-Ala, Ala-Gly-Gly, or any combination thereof.

27. The recombinant vector of claim 1 wherein the vector is maintained in a cell at least 1.5 times more efficiently than a corresponding vector having as its origin of DNA synthesis SEQ ID NO:10.

28. The recombinant vector of claim 1 wherein the vector is maintained in a cell at least 3 times more efficiently than a corresponding vector having as its origin of DNA synthesis SEQ ID NO:10.

29. A method to maintain and express at least one heterologous open reading frame in a cell, comprising: providing a plasmid having the recombinant vector of claim 1 and further comprising a heterologous open reading frame and a DNA segment encoding EBNA-1; and contacting a cell with the plasmid, so as to yield a cell that maintains and expresses the heterologous open reading frame in the plasmid.

30. A method to maintain and express at least one heterologous open reading frame in a cell, comprising: providing a plasmid having the recombinant vector of claim 1 which further comprises a heterologous open reading frame; and contacting a cell which expresses EBNA-1 with the plasmid, so as to yield a cell that maintains and expresses the heterologous open reading frame in the plasmid.

31. The method of claim 29 or 30 wherein the EBNA-1 is a less cytotoxic derivative of the corresponding wild-type protein, which derivative lacks sequences present in the corresponding wild-type protein which activate transcription from an integrated template, and which derivative activates transcription of the heterologous open reading frame at levels at least 5% that of the corresponding wild-type protein.

32. The method of claim 29 or 30 wherein the cell is an embryonic stem cell.

33. The method of claim 29 or 30 wherein the heterologous open reading frame encodes Oct3, Oct4, Sox2, Klf4, C-myc, NANOG, LIN28, or any combination thereof.

34. The method of claim 29 or 30 wherein the cell expresses recombinant Oct3, Oct4, Sox2, Klf4, C-myc, NANOG, LIN28, or any combination thereof.

35. The method of claim 29 or 30 wherein the recombinant plasmid further comprises a selectable marker.

36. The method of claim 35 further comprising selecting for cells that express the selectable marker.

37. A method to prepare a library, comprising:
  a) providing a plurality of isolated DNA molecules;
  b) introducing the plurality of isolated DNA molecules into the recombinant vector of claim 1 so as to provide a library of DNA molecules.

38. A library prepared by the method of claim 37.

39. A method to prepare a cell based library comprising introducing the library of claim 38 to cells and identifying cells with at least one of the recombinant vectors.

40. A host cell comprising the recombinant vector of claim 1.

41. A host cell comprising the recombinant vector of claim 25, wherein one expression cassette encodes a therapeutic gene product.

42. The host cell of claim 41 which is a bone marrow cell.

43. The host cell of claim 41 which is a pluripotent stem cell.

* * * * *